(12) United States Patent
Figeys et al.

(10) Patent No.: US 10,001,493 B2
(45) Date of Patent: Jun. 19, 2018

(54) MARKERS FOR INFLAMMATORY BOWEL DISEASE

(71) Applicant: UNIVERSITY OF OTTAWA, Ottawa (CA)

(72) Inventors: Daniel Figeys, Ottawa (CA); Alain Stintzi, Ottawa (CA); David R. Mack, Ottawa (CA); Cheng-Kang Chiang, Ottawa (CA); Amanda Elizabeth Starr, Ottawa (CA)

(73) Assignee: UNIVERSITY OF OTTAWA, Ottawa, ON (CA)

( * ) Notice: Subject to any disclaimer, the term of this patent is extended or adjusted under 35 U.S.C. 154(b) by 0 days. days.

(21) Appl. No.: 15/477,508

(22) Filed: Apr. 3, 2017

(65) Prior Publication Data
US 2017/0205429 A1 Jul. 20, 2017

Related U.S. Application Data

(63) Continuation-in-part of application No. PCT/CA2015/050992, filed on Oct. 2, 2015.

(60) Provisional application No. 62/059,316, filed on Oct. 3, 2014.

(51) Int. Cl.
*G01N 33/68* (2006.01)

(52) U.S. Cl.
CPC ..... *G01N 33/6893* (2013.01); *G01N 2333/47* (2013.01); *G01N 2333/902* (2013.01); *G01N 2333/914* (2013.01); *G01N 2333/91142* (2013.01); *G01N 2800/065* (2013.01)

(58) Field of Classification Search
None
See application file for complete search history.

(56) References Cited

U.S. PATENT DOCUMENTS

| | | | |
|---|---|---|---|
| 5,039,703 A * | 8/1991 | Breuer | A61K 31/19 514/557 |
| 5,225,329 A | 7/1993 | Marks | |
| 2015/0125439 A1* | 5/2015 | Schuchman | A61K 9/0073 424/94.6 |

OTHER PUBLICATIONS

Carter et al., Guidelines for the management of inflammatory bowel disease in adults, Gut 2004; 53 (Suppl V): v1 -v16.*
Neubauer et al.; "Vistafin/PBEF/Nampt and other adipocytokines in inflammatory bowel disease", Adv. Clin. Exp. Med., vol. 19, 2010, pp. 399-404.
PCT/CA2015/050992 international search report, dated Dec. 10, 2015.
PCT/CA2015/050992 search strategy, dated Dec. 10, 2015.
PCT/CA2015/050992 written opinion, dated Jan. 18, 2016.

* cited by examiner

*Primary Examiner* — Gary Counts
(74) *Attorney, Agent, or Firm* — Anglehart et al.

(57) ABSTRACT

There is provided protein biomarkers and methods for their use in diagnosing and treating Inflammatory Bowel Disease (IBD), ulcerative colitis (UC) and Crohn's disease (CD) as well as methods for assessing the severity of the diseases.

7 Claims, 45 Drawing Sheets

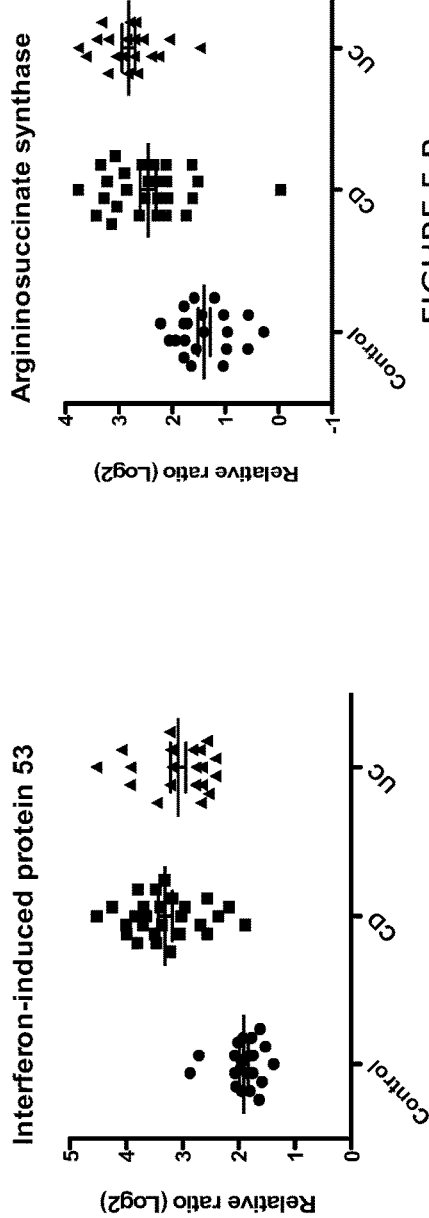
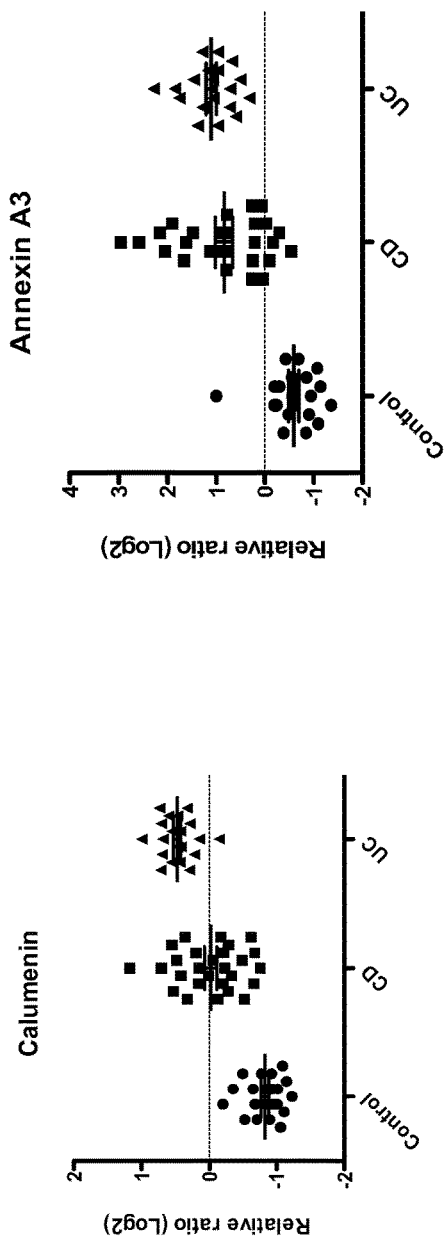
FIGURE 5 A
FIGURE 5 B
FIGURE 5 C
FIGURE 5 D

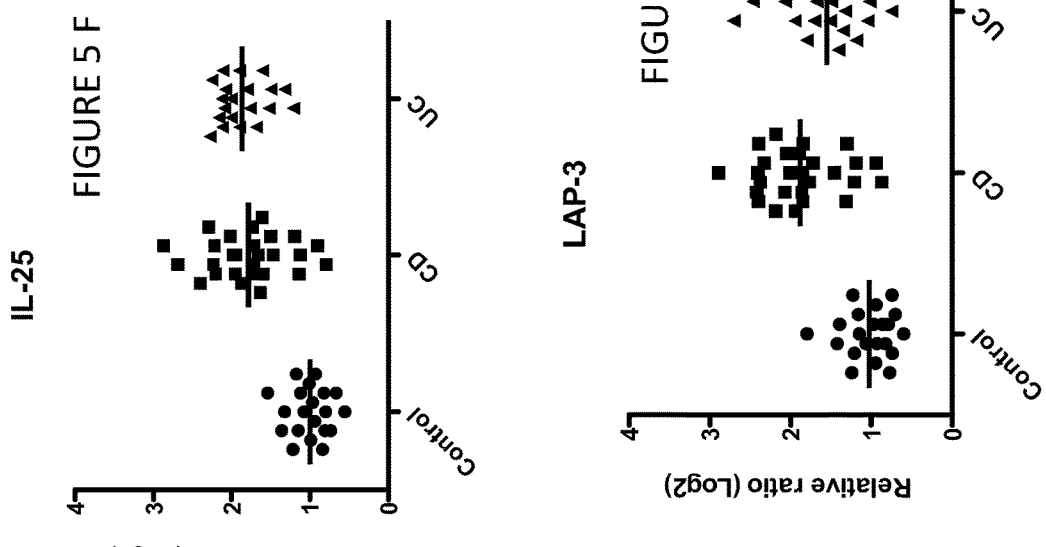
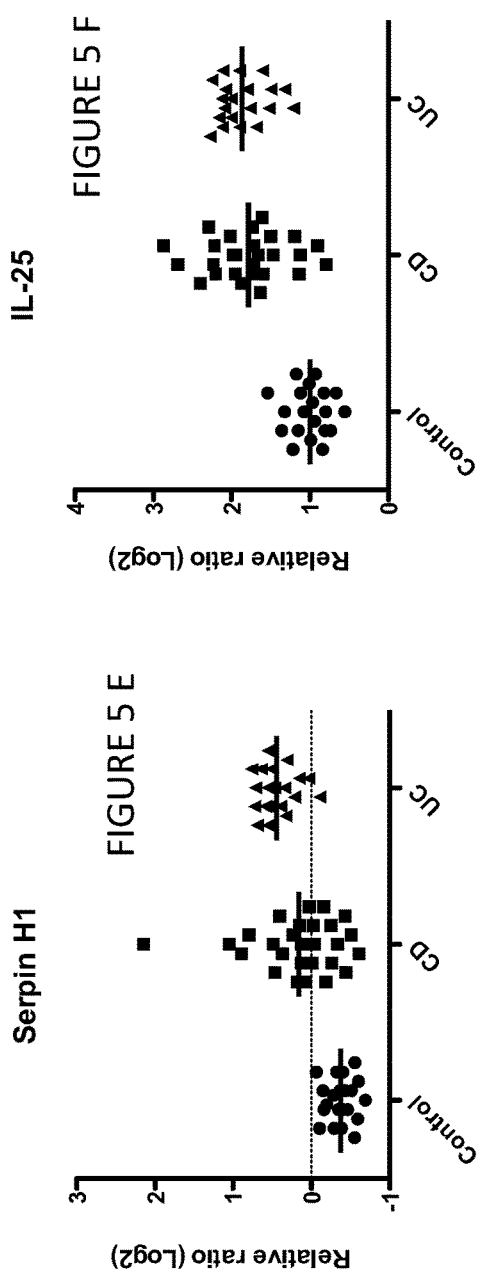
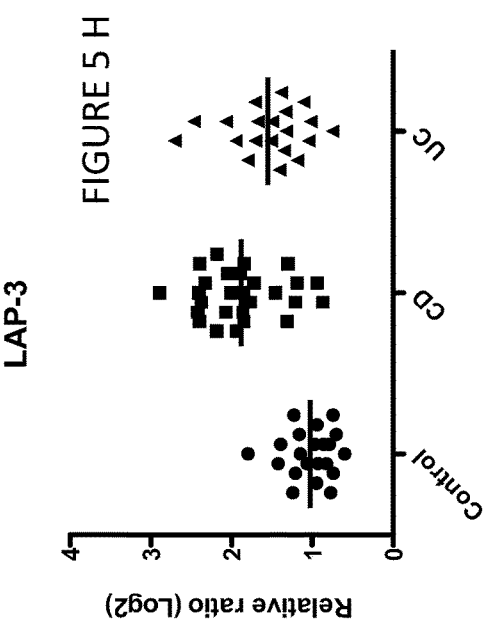
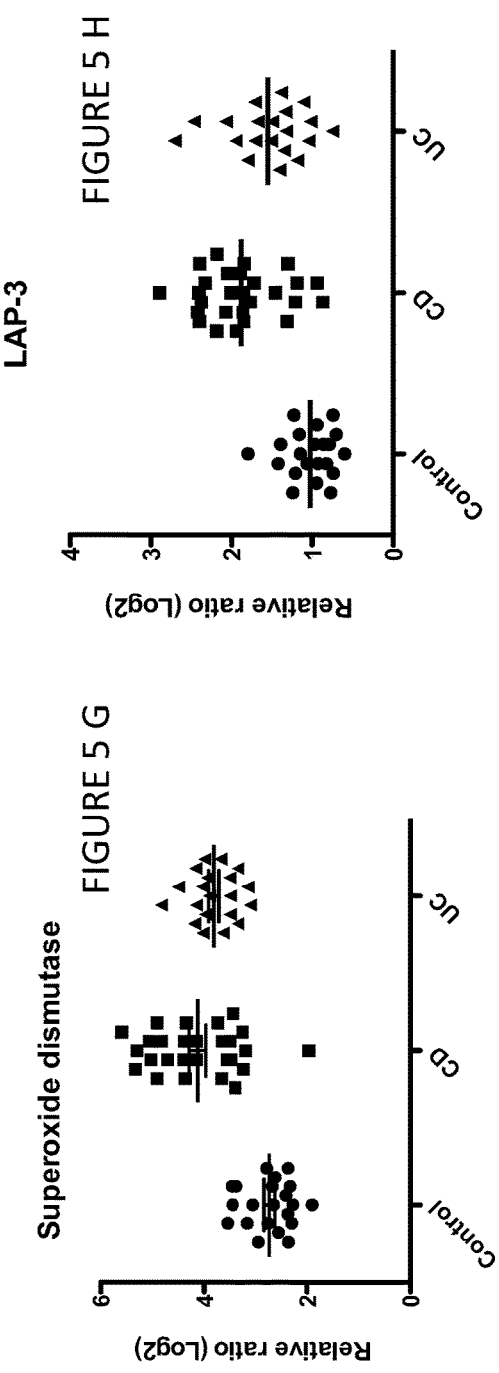

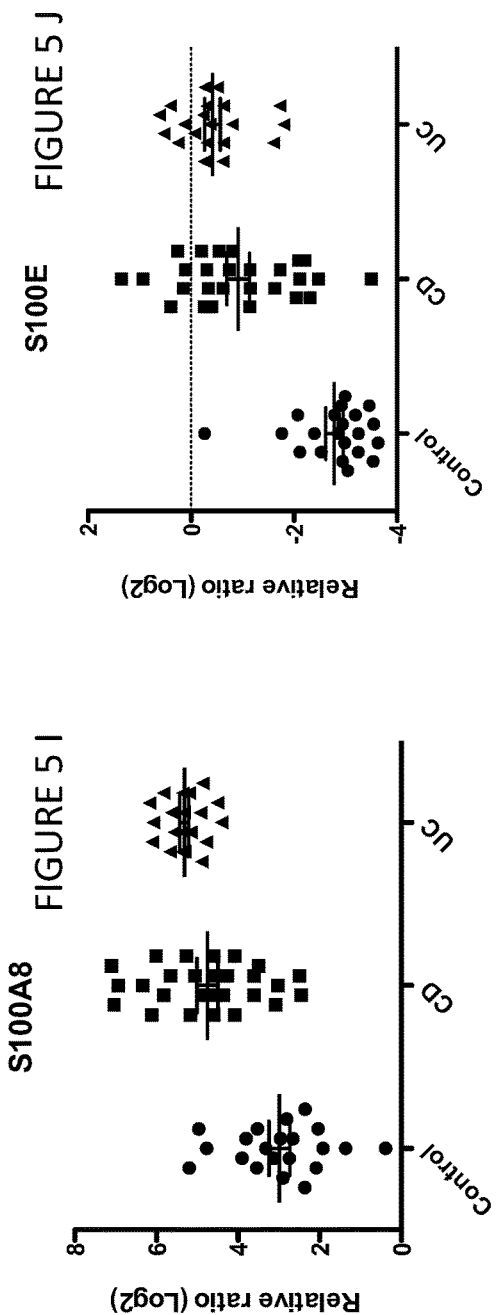
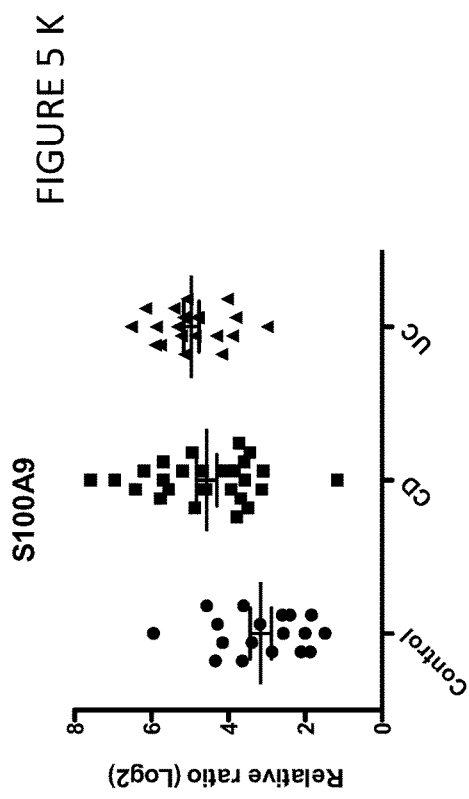
FIGURE 5 I
FIGURE 5 J
FIGURE 5 K

FIGIGURE 6

Leucine Aminopeptidase 3
(LAP3)

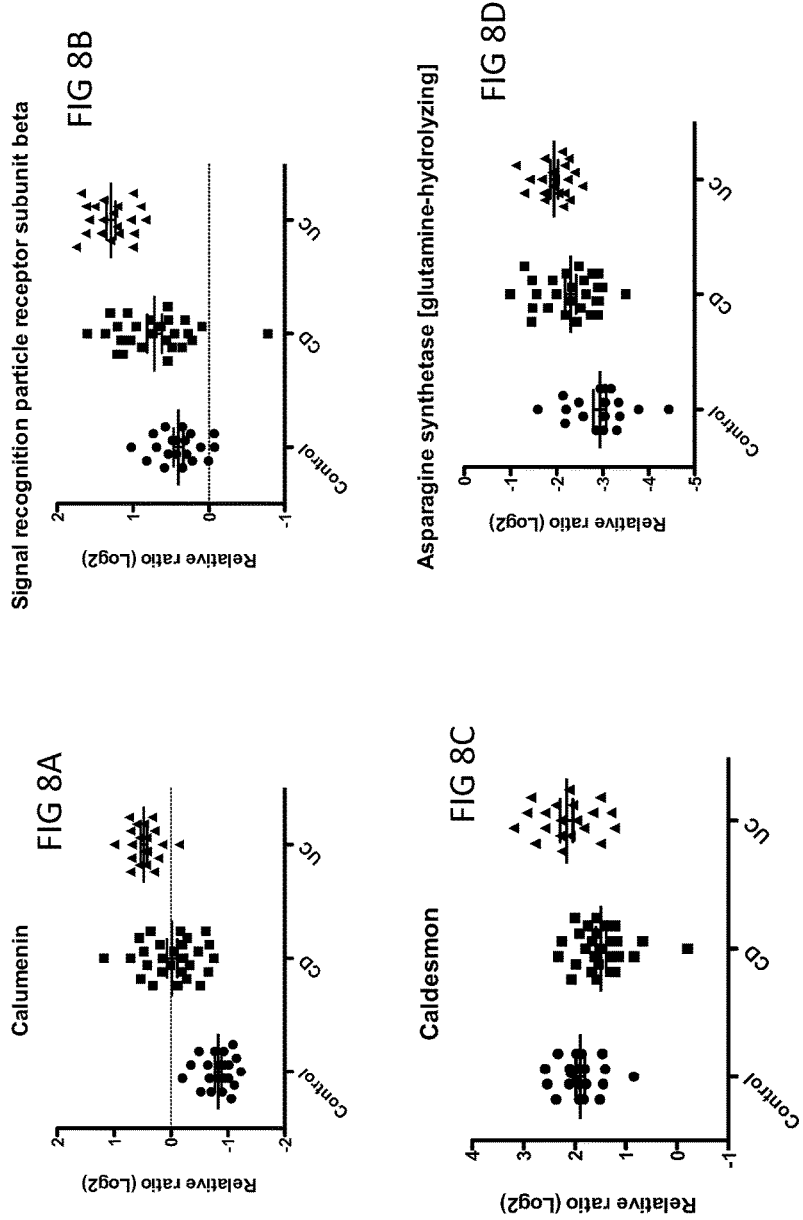

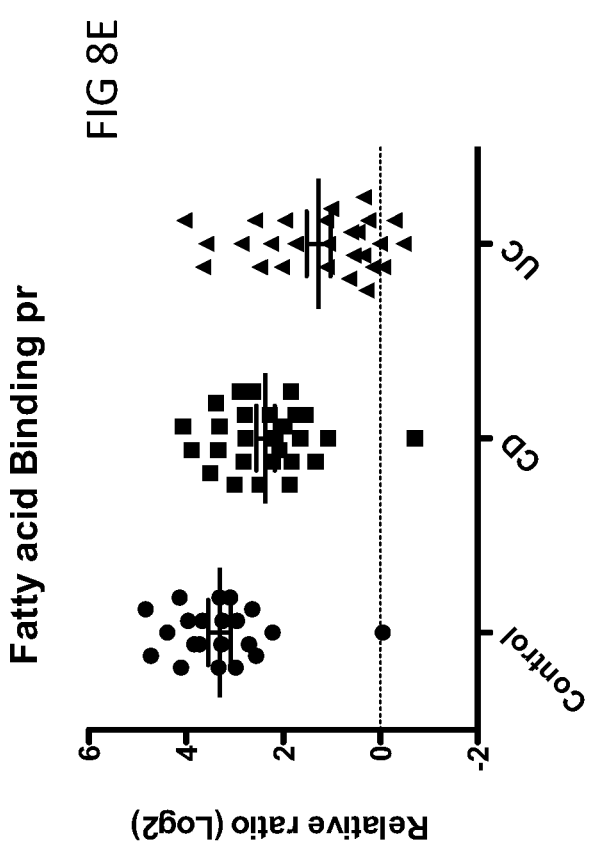

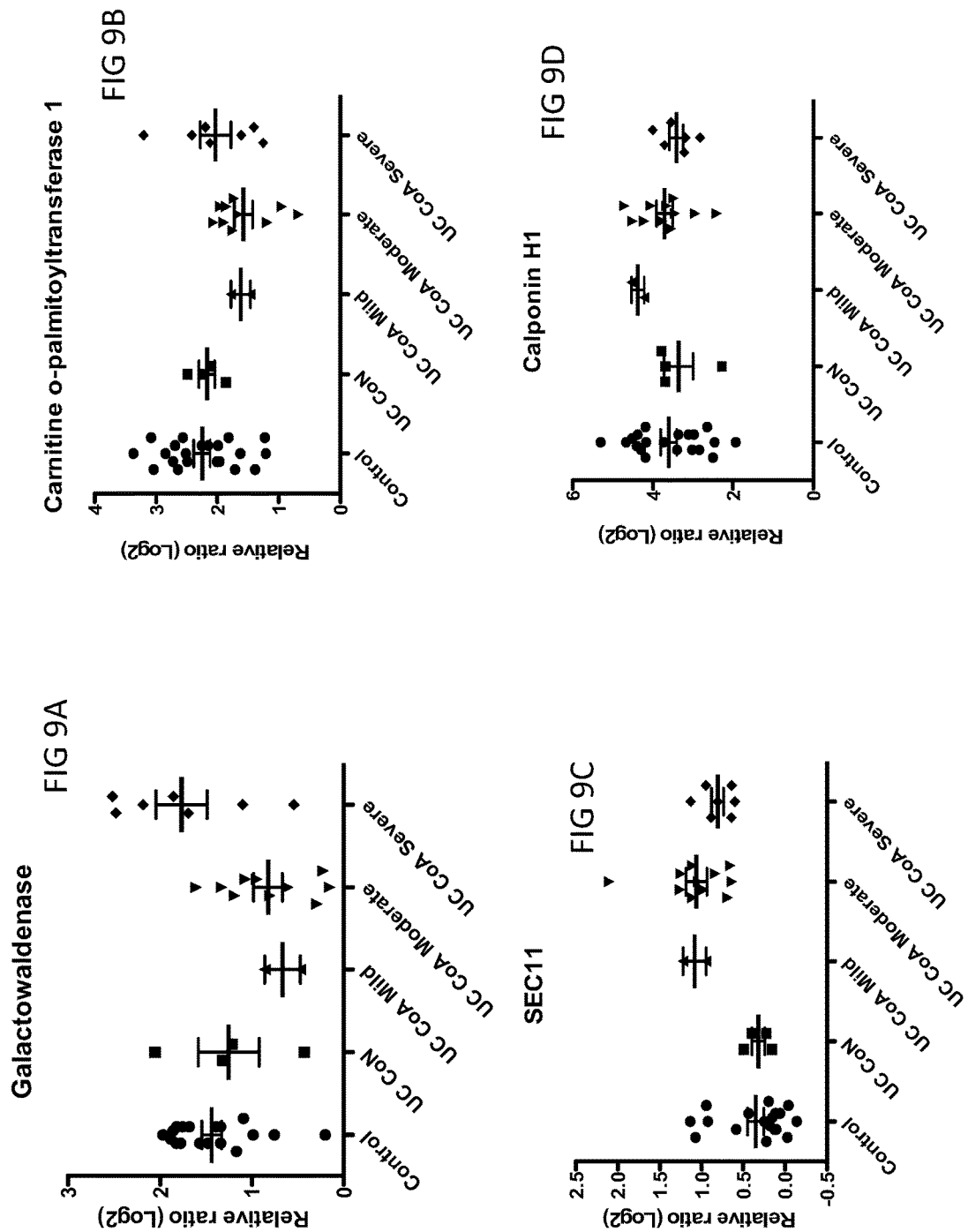

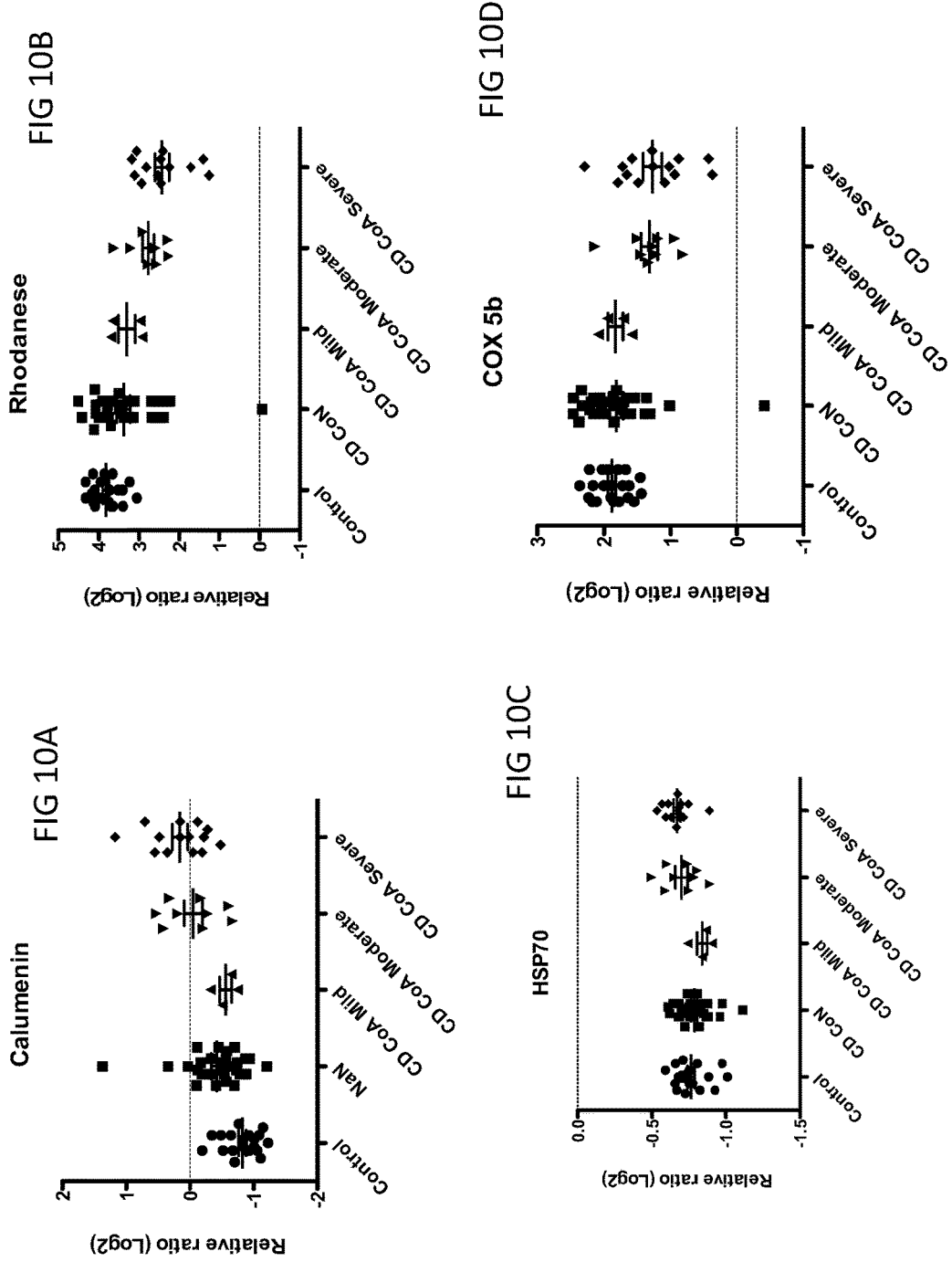

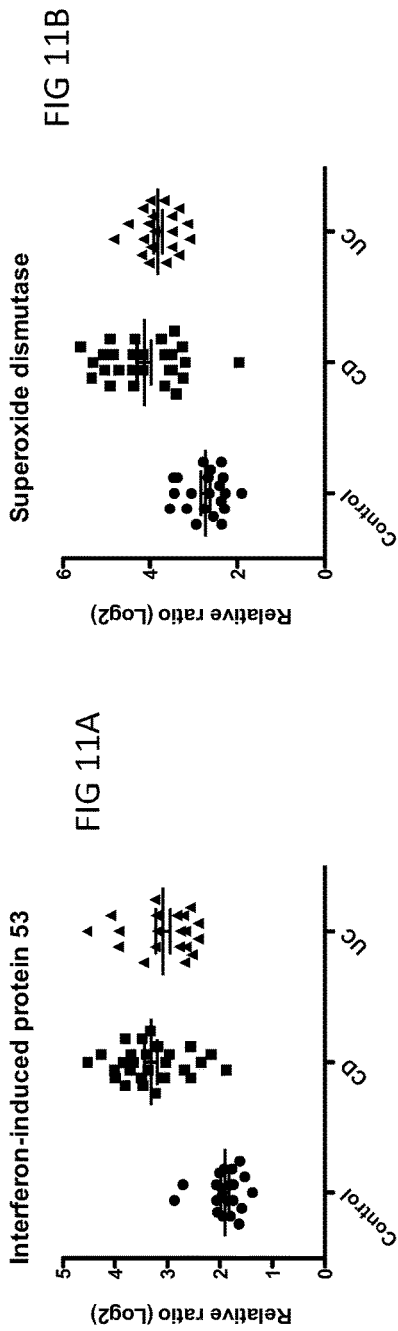
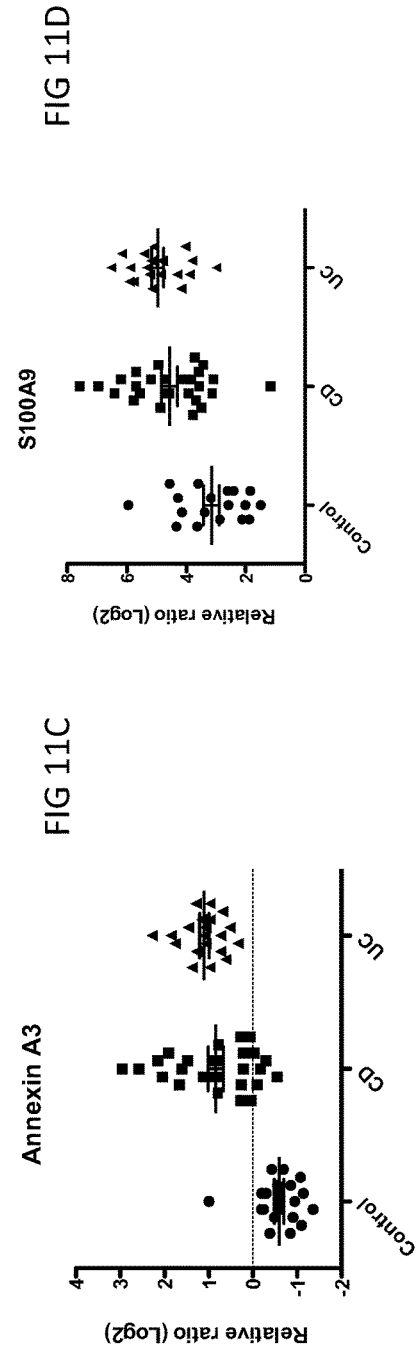

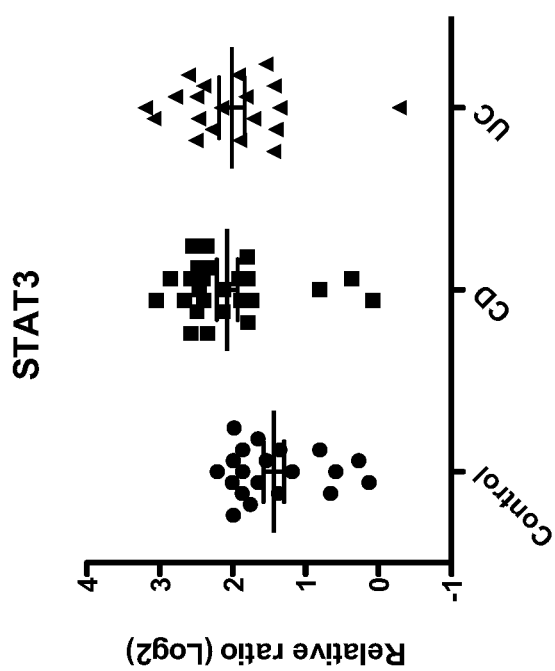

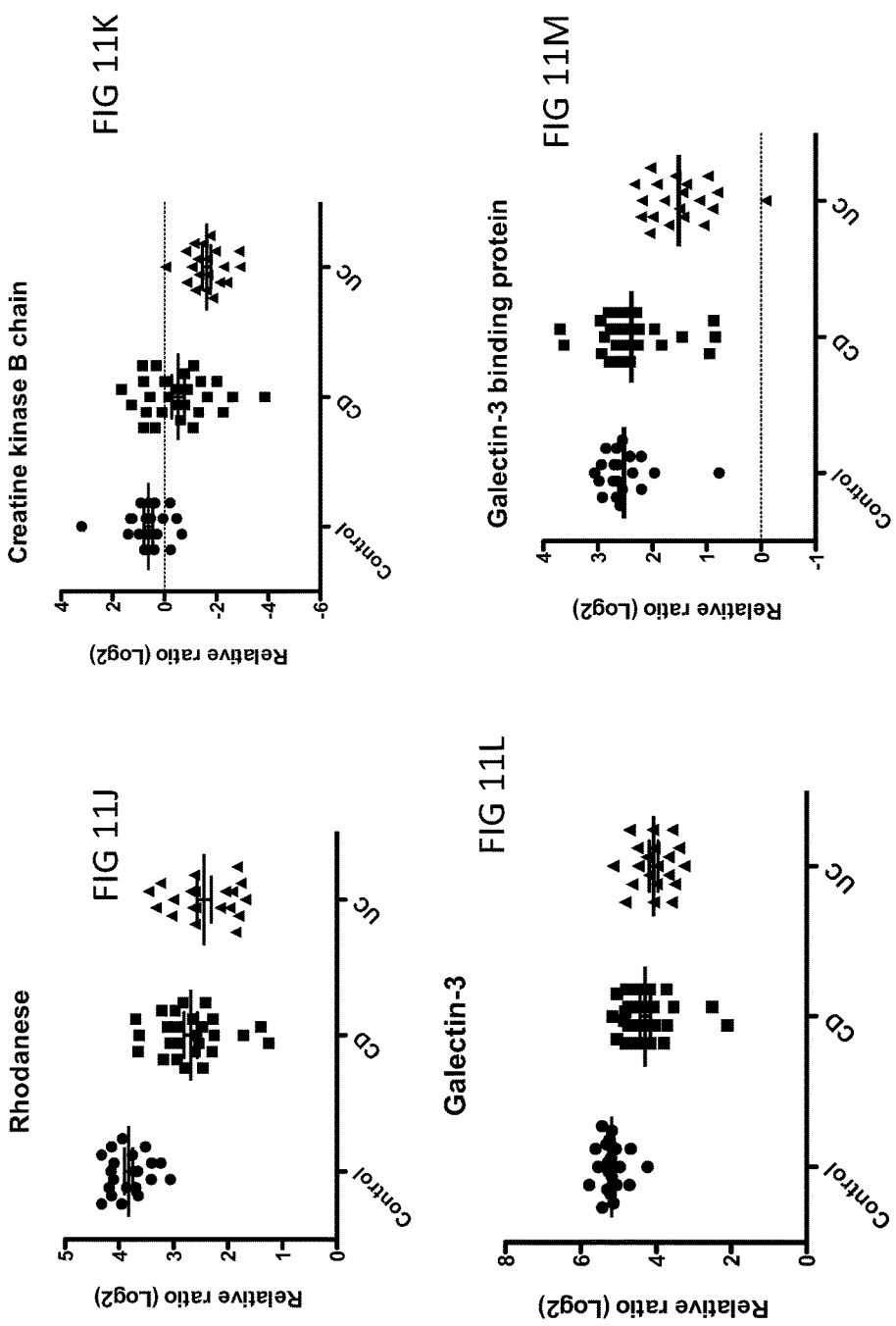

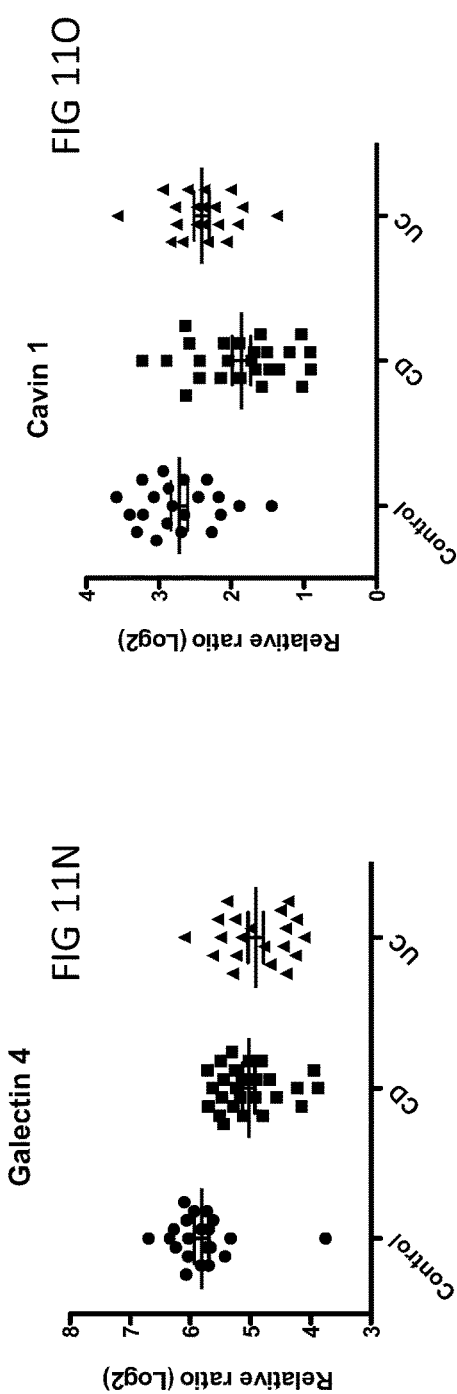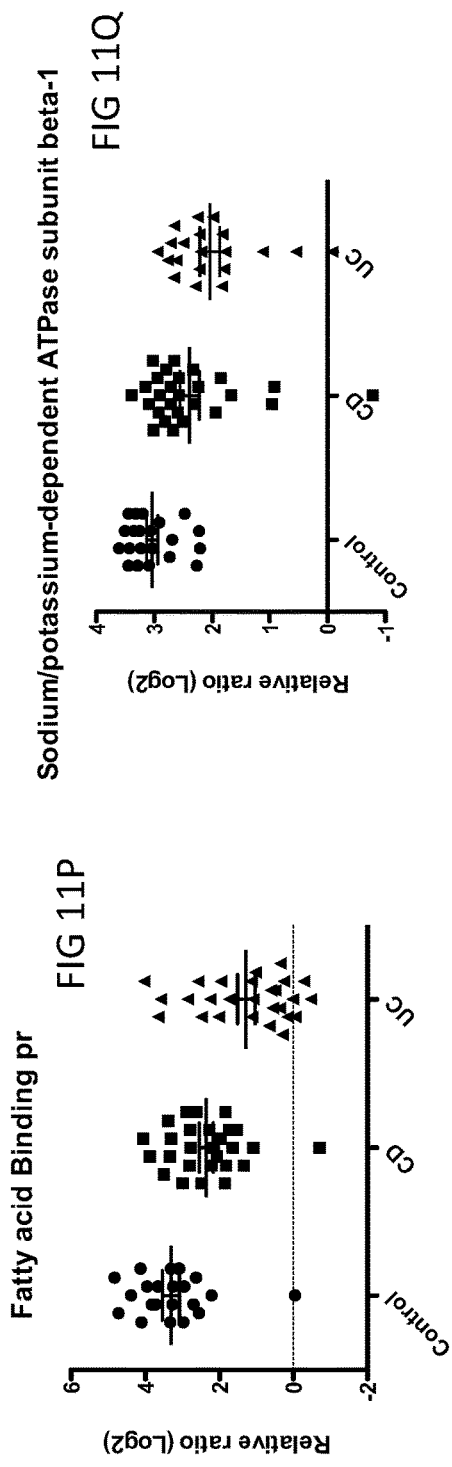

Control vs CD vs UC (Ttest): PCA loading
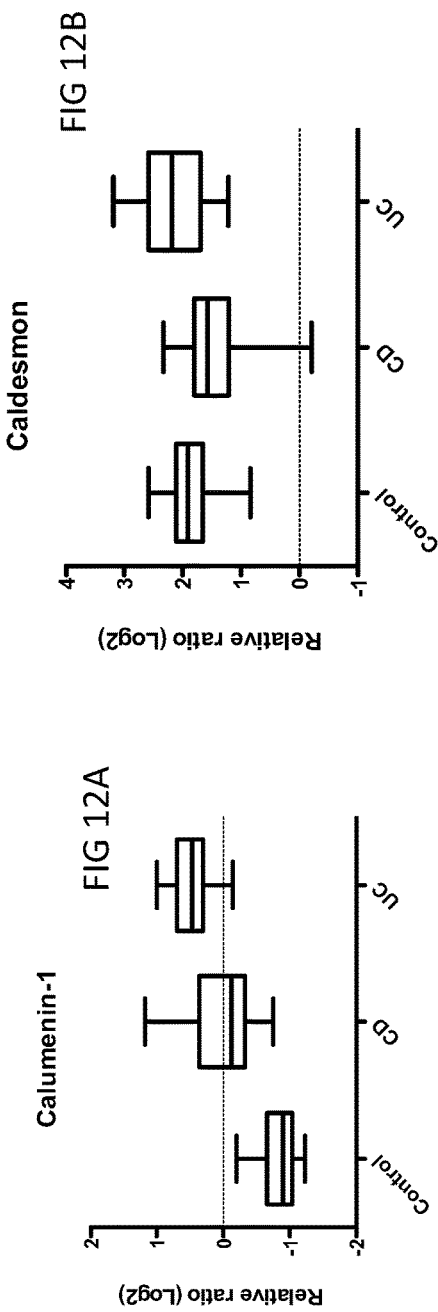
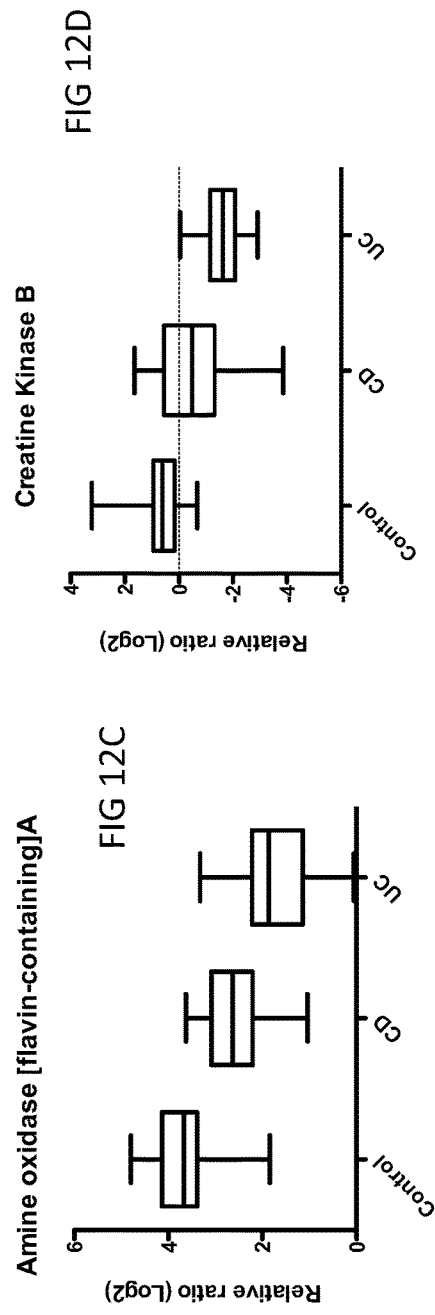
FIG 12A — Calumenin-1
FIG 12B — Caldesmon
FIG 12C — Amine oxidase [flavin-containing]A
FIG 12D — Creatine Kinase B

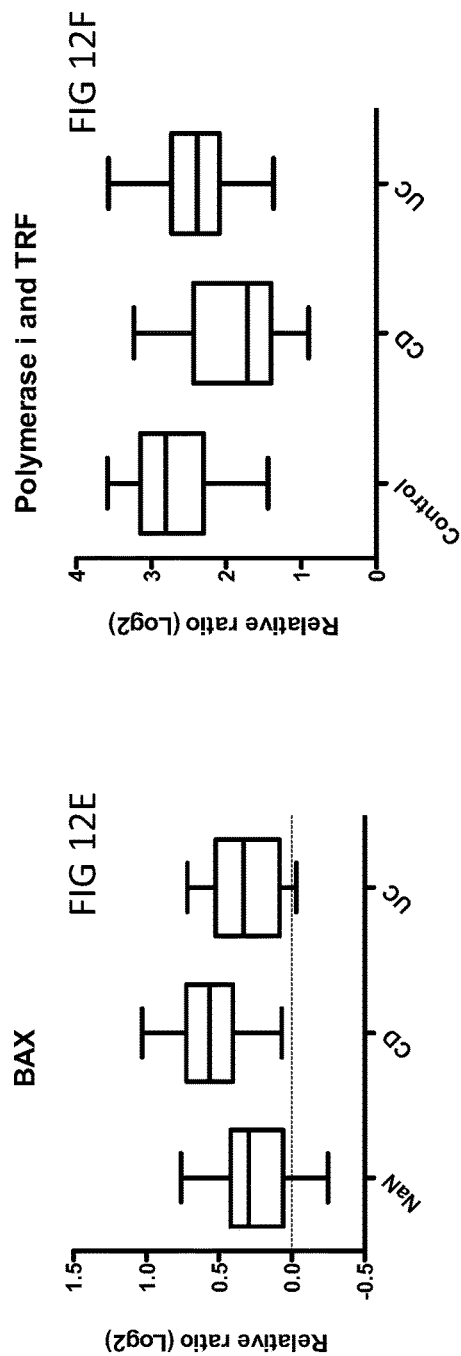
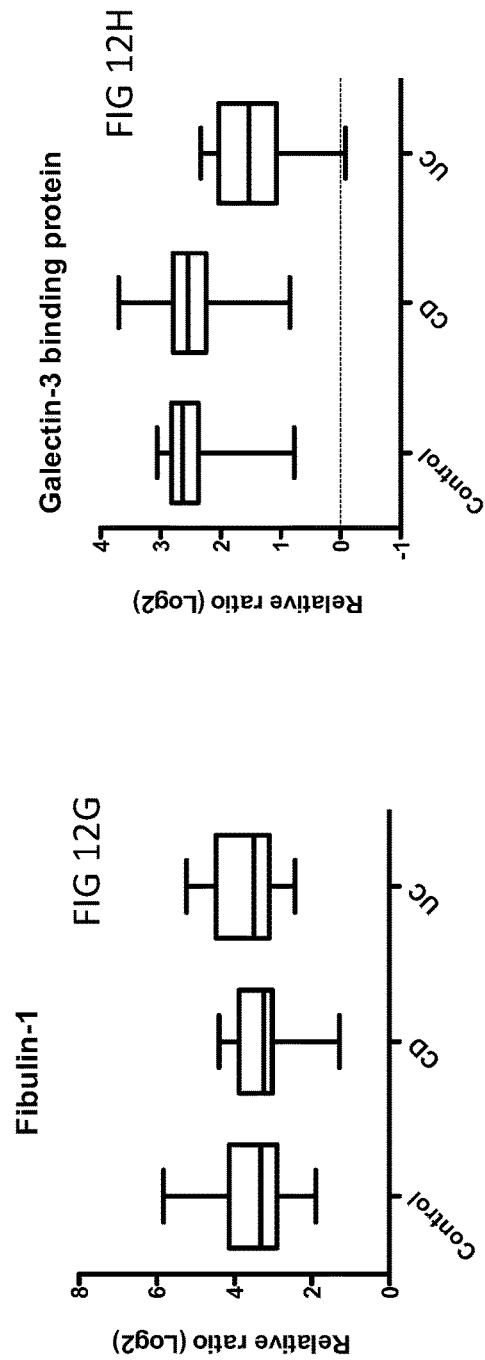

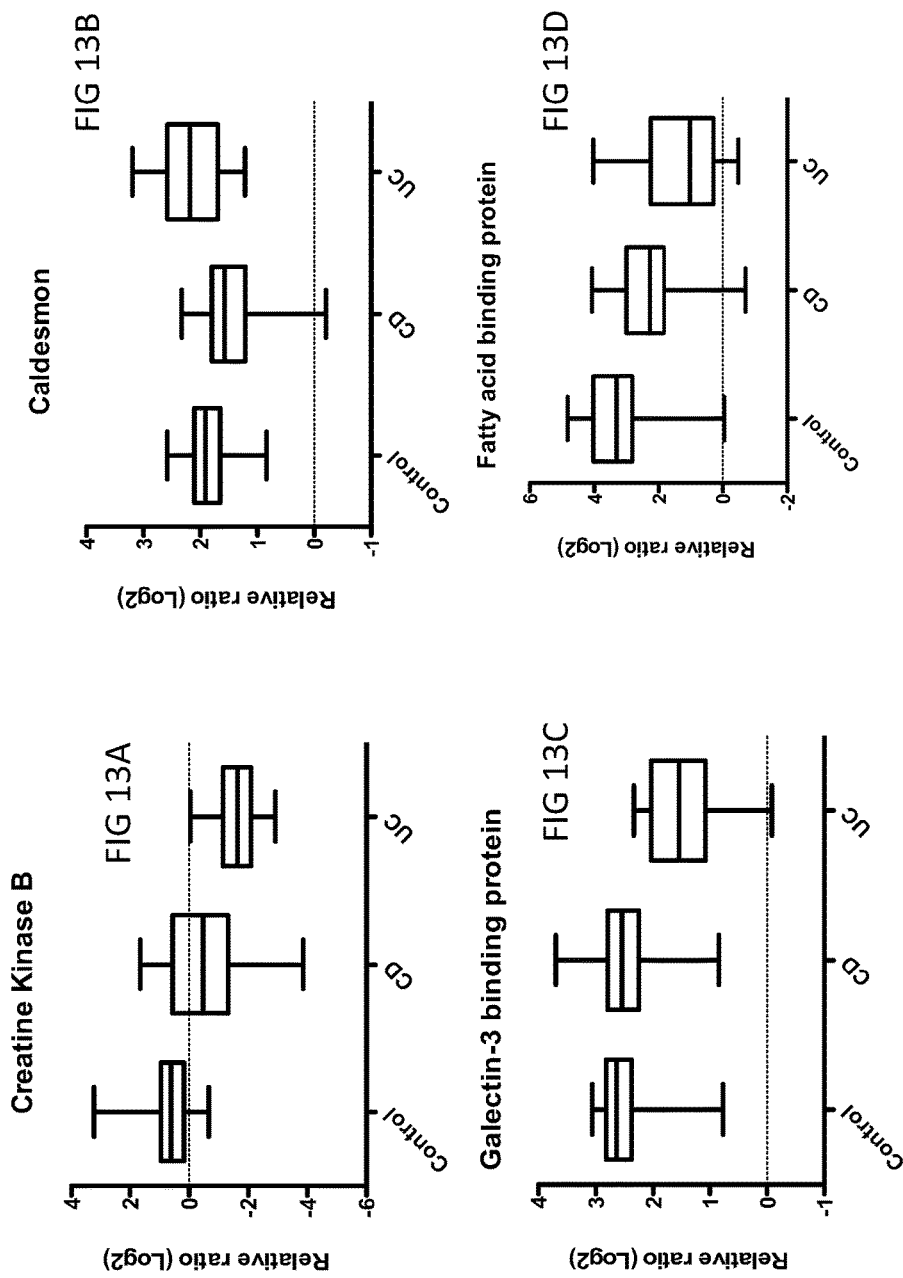

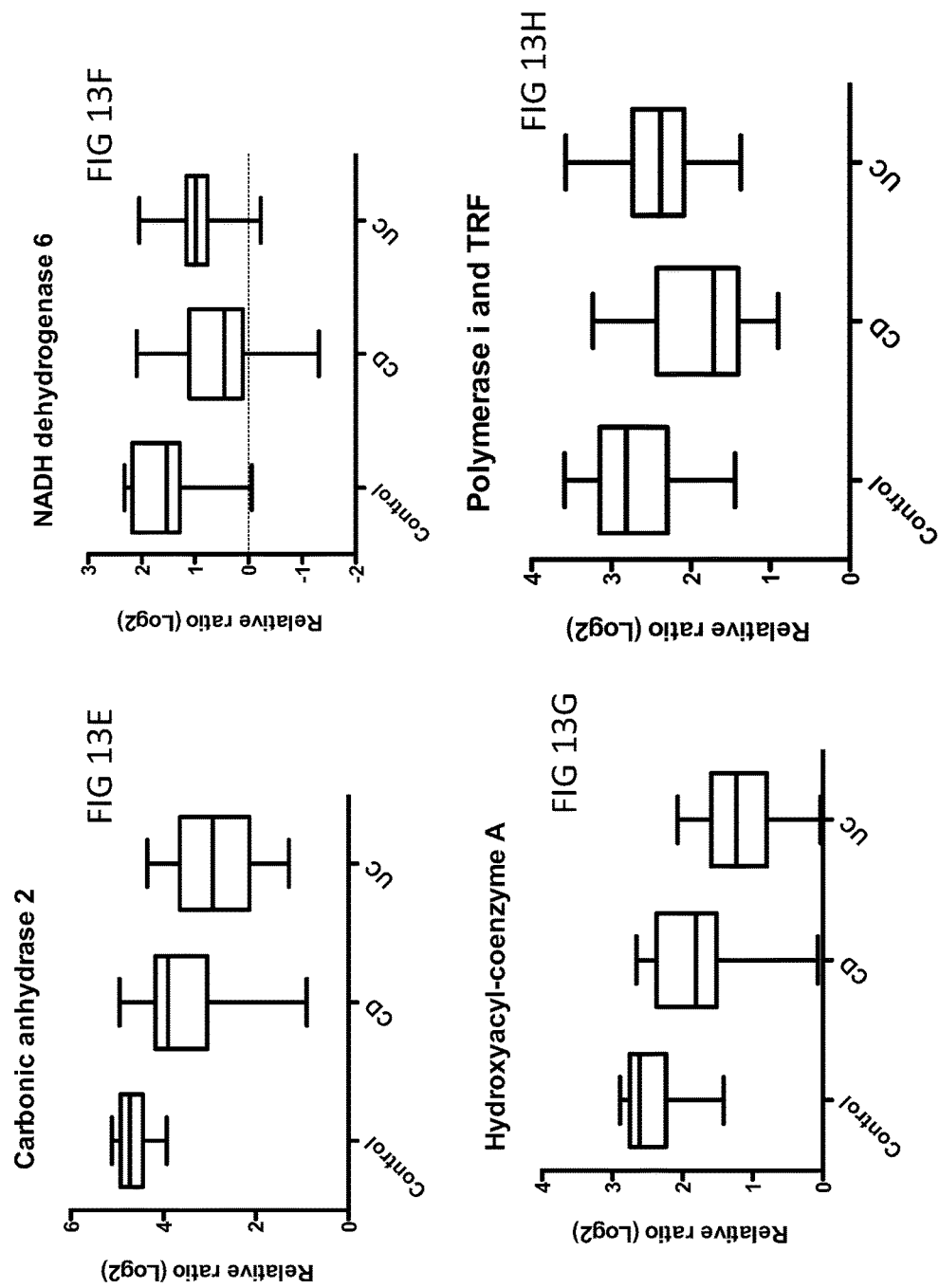

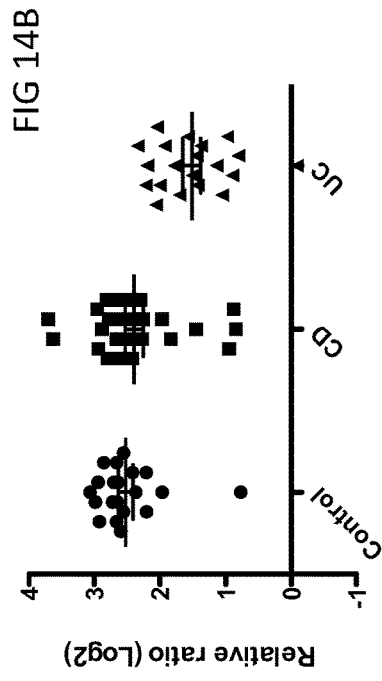
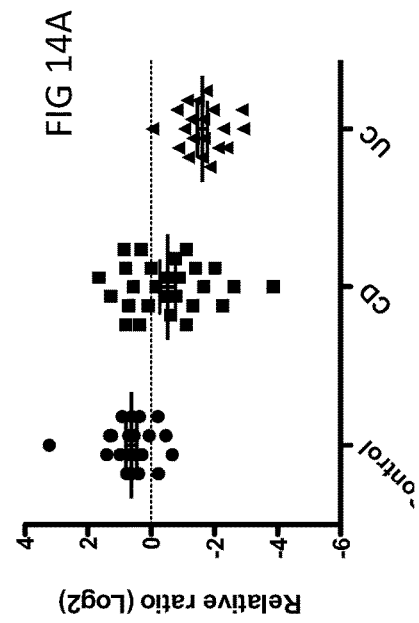
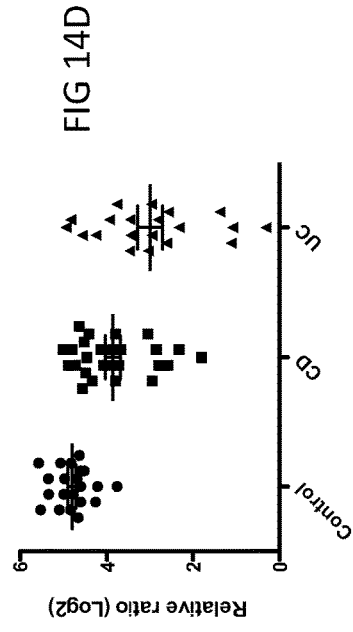
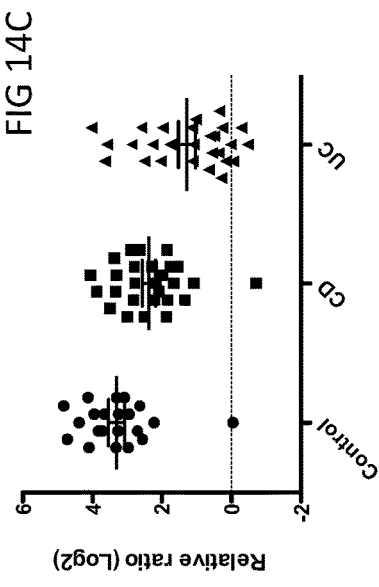
UC vs CD PLSDA– High in CD
FIG 14A Creatine kinase B chain
FIG 14B Galectin-3-binding pr
FIG 14C Fatty acid Binding pr
FIG 14D Calcium-activated chloride channel family member 1

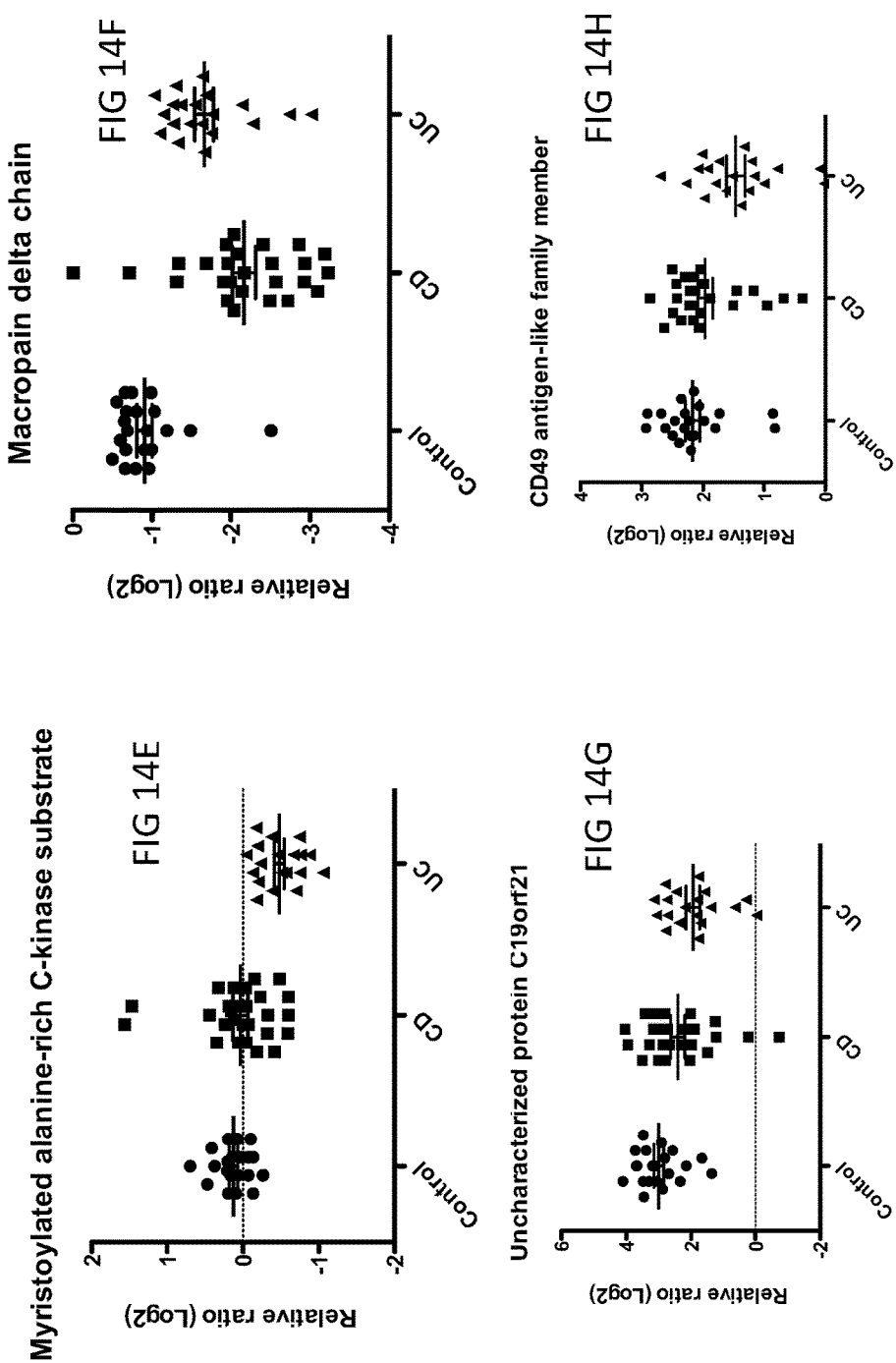

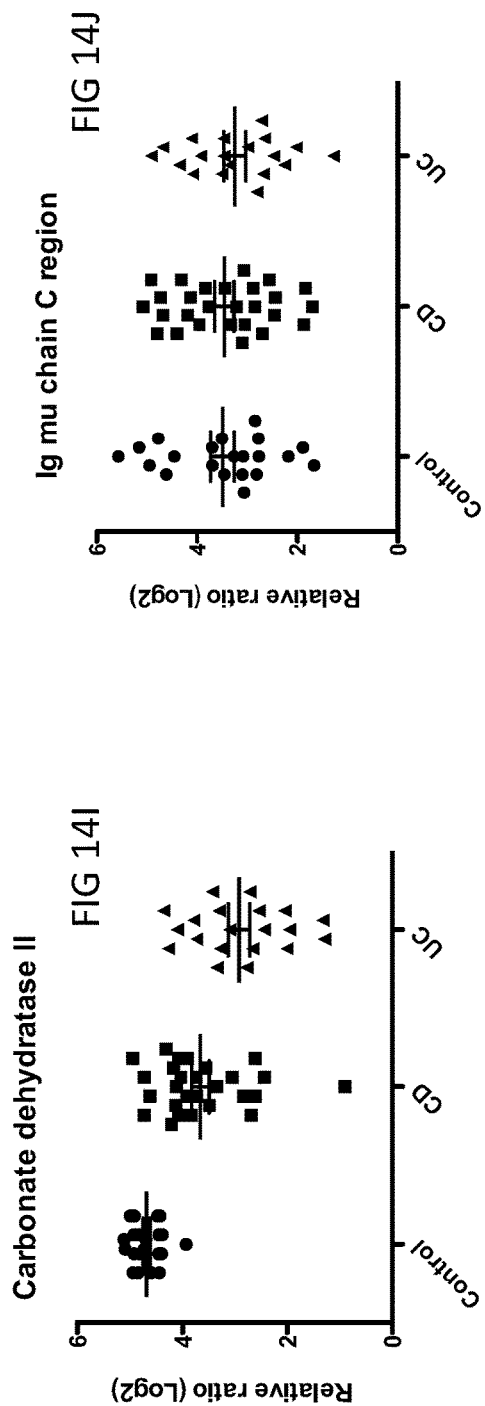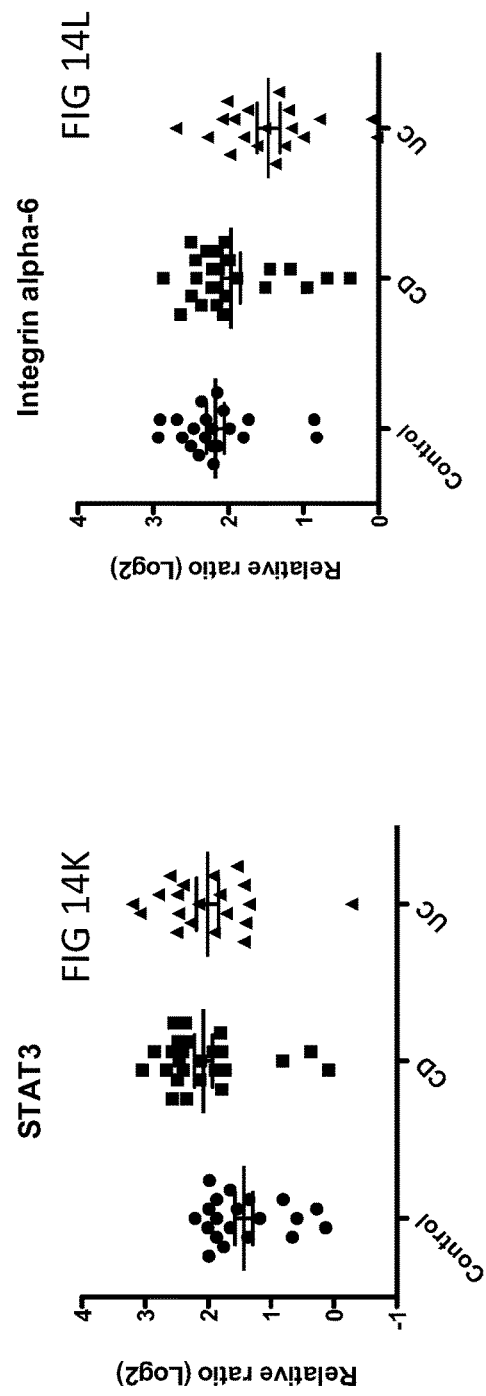

UC vs CD PLSDA— High in UC

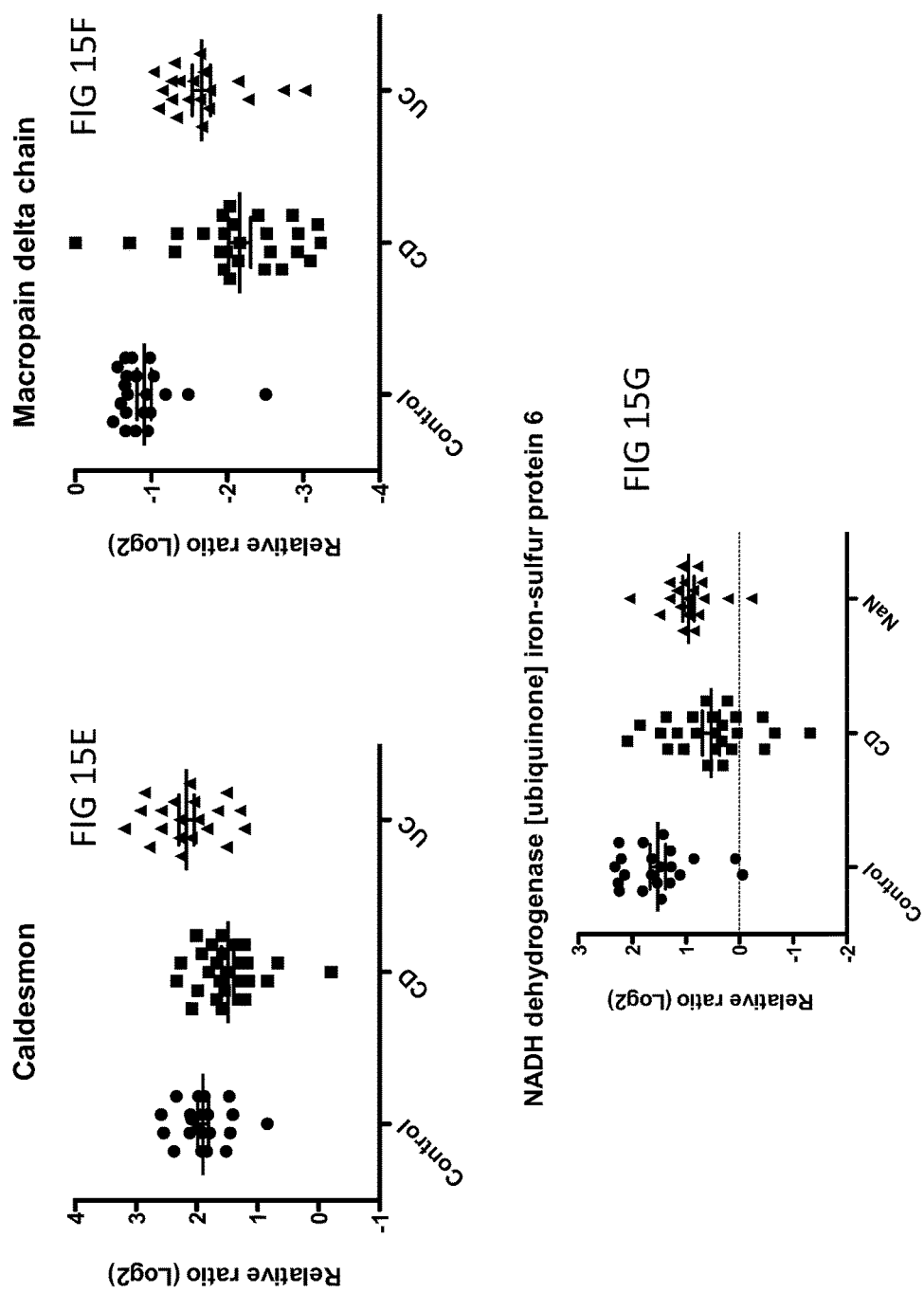

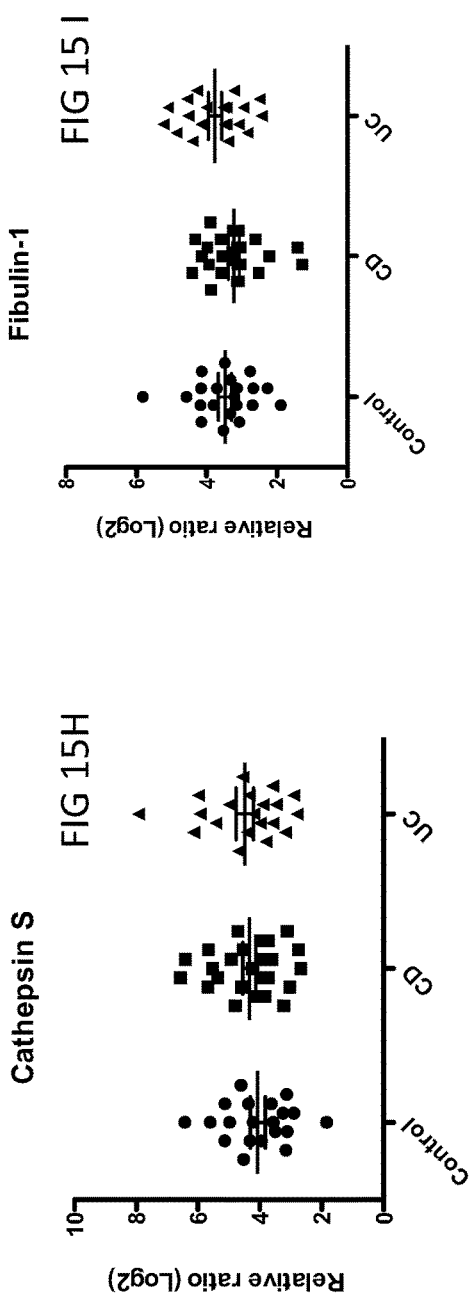
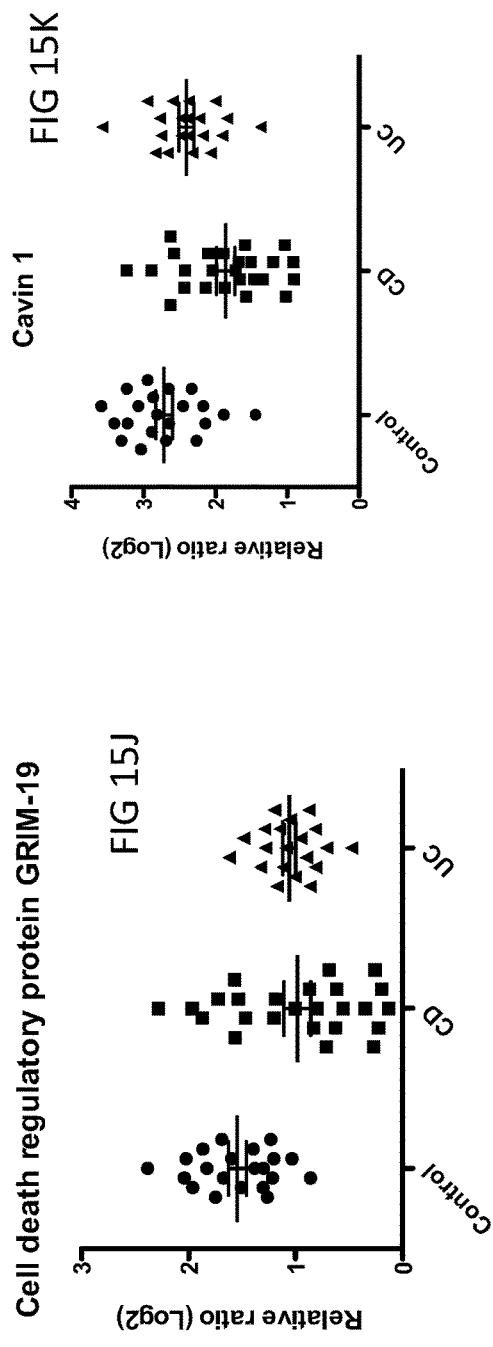

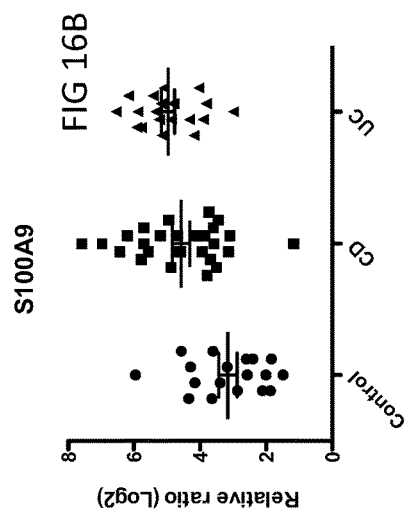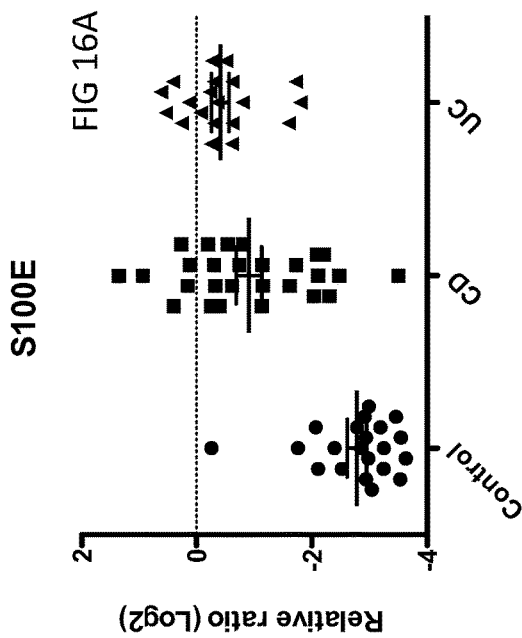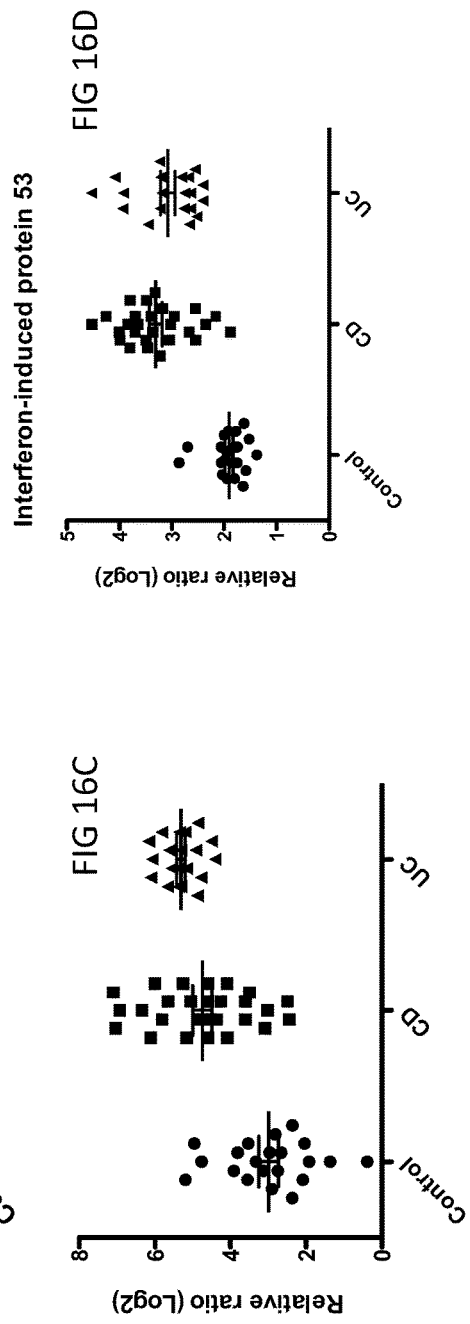

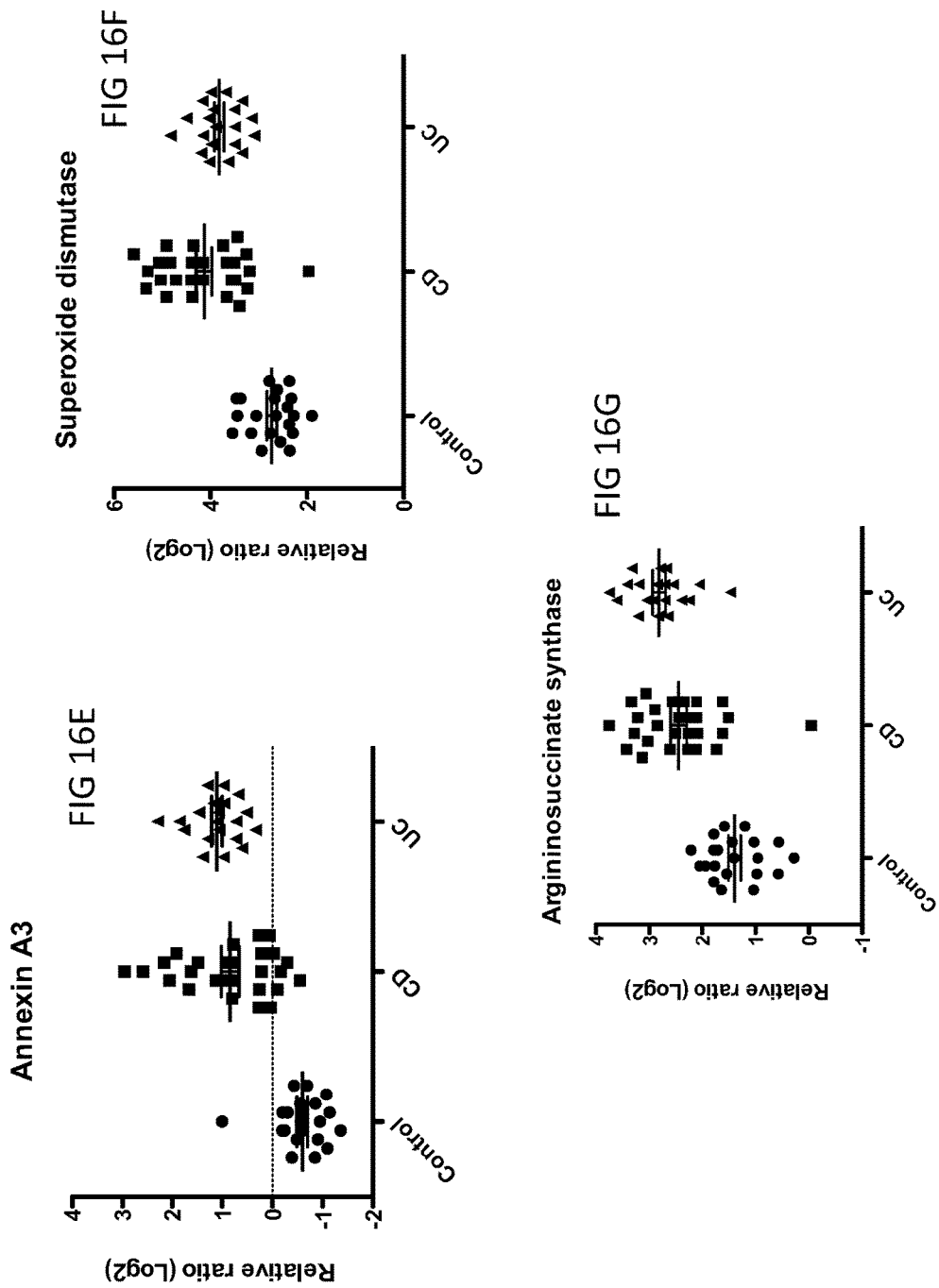

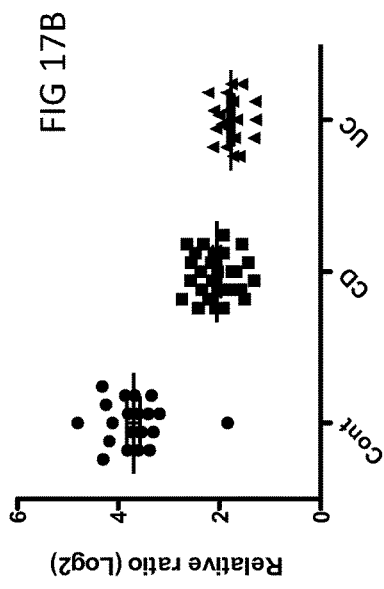
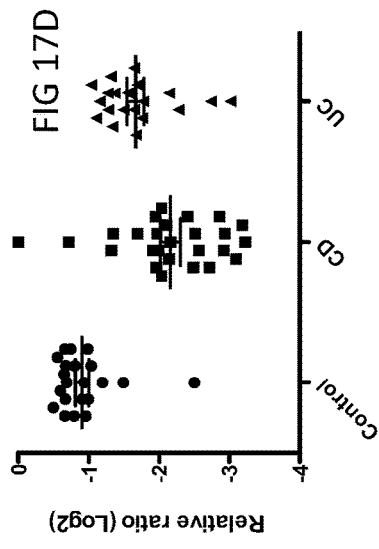
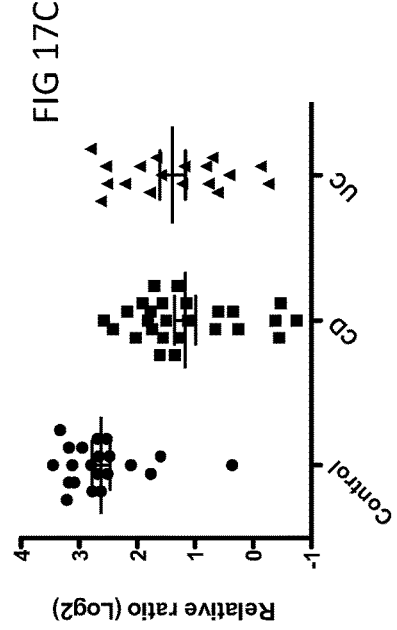

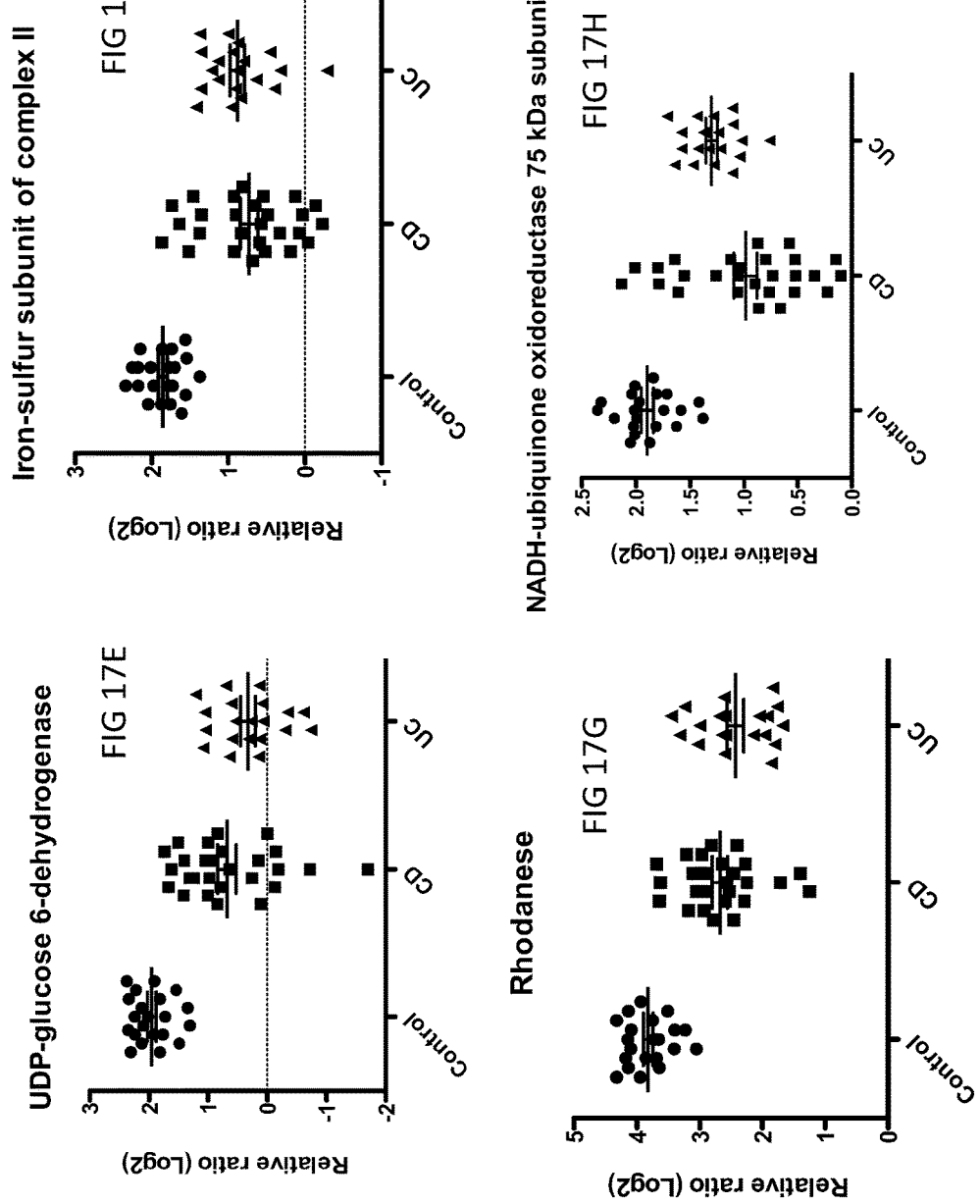

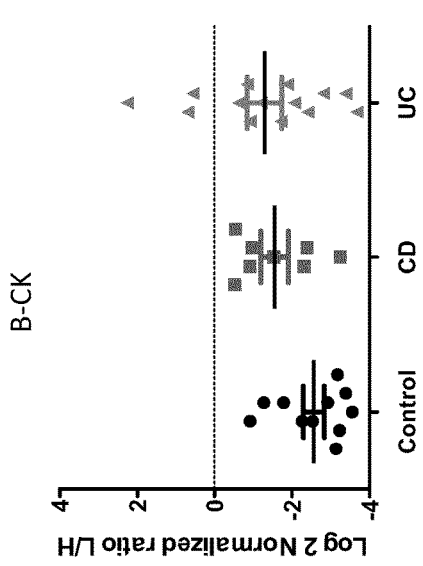
FIG 18C
FIG 18D
FIG 18E

Superoxide Dismutase

IL25

Calumenin

Leucine Aminopeptidase 3

MARKERS FOR INFLAMMATORY BOWEL DISEASE

This application is a continuation-in-part of PCT/CA2015/050992 and claims priority of PCT/CA2015/050992 filed Oct. 2, 2015 designating the United States and which claims priority of U.S. provisional application 62/059,316 filed on Oct. 3, 2014.

TECHNICAL FIELD

This invention relates generally to protein markers for inflammatory bowel disease (IBD), ulcerative colitis (UC) and Crohn's disease (CD) classification.

BACKGROUND

Inflammatory Bowel Disease encompasses two principal conditions: ulcerative colitis (UC) and Crohn's disease (CD). Some patients have features of both subtypes and are classified as IBD-undefined (IBD-U) (Gastroenterology, 2007. 133(5): p. 1670-89). UC is defined by continuous mucosal inflammation starting in the rectum and restricted to the colon while CD inflammation can occur anywhere in the gastrointestinal tract, involves full thickness of the bowel wall and often with skip lesions (Gastroenterol Clin North Am, 2009. 38(4): p. 611-28; Gastroenterology, 2007. 133(5): p. 1670-89). Recent attempts to find new markers for IBD subtypes, such as conventional antibodies, have fared very poorly at differentiating colonic CD versus UC. As treatments and responses to medical therapies differ between CD and UC (J Pediatr Gastroenterol Nutr, 2010, S1-S13. The American journal of gastroenterology, 2011. 106 Suppl 1: p. S2-25; quiz S26. Gastroenterol Clin North Am, 2009. 38(4): p. 611-28) there is an urgent need for biomarkers to differentiate between CD and UC.

The primary tool used for both diagnosis and IBD management is endoscopy (World J Gastrointest Endosc, 2012. 4(6): p. 201-11). Endoscopy enables both visualization of the mucosa and access for mucosal biopsies to diagnose disease, to define disease extent and activity, and to monitor disease progression. The diagnostic accuracy from colonoscopy ranges from 60 to 74% (J Clin Pathol, 2002. 55: p. 955-60). Other diagnostic approaches include radiological imaging and histological examination of mucosal biopsies in the differentiation of IBD subtypes (e.g non-caseating submucosal granuloma). However, 10% of patients (Registry. Dtsch Arztebl Int 2015; 112:121-7) have ambiguous diagnosis using these approaches and are instead classified as IBD-unclassified (IBD-U) patients (J Pediatr Gastroenterol Nutr 2014; 58:795-806). Accurate and early diagnosis is essential for proper disease management. The goal of IBD treatment is to bring active disease into remission and to prevent follow-up relapse (flare-ups). The choice of treatment depends on disease subtype (CD versus UC), disease location, severity of disease, disease complications and individual host factors (e.g. nutritional and growth status, pubertal status, child's age and size, medication allergies) (J Pediatr Gastroenterol Nutr, 2010, S1-S13. The American journal of gastroenterology, 2011. 106 Suppl 1: p. S2-25; quiz S26. Gastroenterol Clin North Am, 2009. 38(4): p. 611-28). Current drug therapies consist of aminosalycylates, immune-modulators, corticosteroids, antibiotics and biological therapies (i.e. anti-TNFα monoclonal antibodies). The optimum therapeutic regimen for maintaining a disease free state still remains to be determined and the effectiveness of these drugs significantly differs between CD and UC (J Pediatr Gastroenterol Nutr, 2010, S1-S13. The American journal of gastroenterology, 2011. 106 Suppl 1: p. S2-25; quiz S26. Gastroenterol Clin North Am, 2009. 38(4): p. 611-28). For example, 5-aminosalicylic acid (5-ASA) drugs are moderately effective at inducing remission and preventing relapse in mild-to-moderate-active UC, while they are not recommended in the management of active CD (The American journal of gastroenterology, 2011. 106 Suppl 1: p. S2-25; quiz S26). There is good evidence for use of methotrexate as maintenance therapy to prevent relapse in CD however, there is no evidence for its use in UC (The American journal of gastroenterology, 2011. 106 Suppl 1: p. S2-25; quiz S26). Greater doses of anti-TNFα therapies at more frequent intervals are being just now recognized to be required for successful treatment of severe UC as compared to standard treatment protocols in use for CD. One third of the cost associated with IBD is due to medical therapies (CCFC. 2008, report. p. 1-101) stressing the economic importance of an effective treatment and thereby an accurate diagnosis.

Genome wide association studies in both adults and pediatric patients have identified novel IBD-associated genes but only define 25% of the genetic risk for developing IBD and excepting for very young infants (i.e. <2 years of age), no unique genes have been discovered that define pediatric IBD from adult-onset IBD. IBD is a complex polygenic disease involving multiple risk gene loci (Nature genetics, 2008. 40(8): p. 955-62. Nature genetics, 2009. 41(12): p. 1335-40. Nature genetics, 2010. 42(4): p. 332-7). These loci encode genes involved in innate and adaptive immunity, autophagy, and maintenance of epithelial barrier integrity for those genes that have known function. While these studies have shown us that multiple pathways are involved in the pathogenesis of IBD, we remain surprisingly ignorant on the root cause(s) and pathogenesis of IBD.

Protein biomarkers could complement current IBD diagnostic tools by reducing ambiguous diagnosis of IBD, subtype differentiation and may also deliver insight into the disease course. Previous studies have identified proteins that are elevated and measurable in serum or stool, however the clinical relevance of these proteins in diagnosis of IBD-U patients is limited, and have been found to perform best in more obvious cases of CD or UC in the pediatric population (Pediatrics 2010; 125:1230-6; Inflamm Bowel Dis 2012; 18:1493-7). Serum detected antibodies directed against neutrophil or bacterial components tend to have low sensitivities (true positive rate <50%). Other biomarkers are now becoming available, namely fecal calprotectin, which are clinically useful to identify IBD patients from populations without mucosal inflammation (e.g. irritable bowel syndrome (IBS), healthy controls), but cannot differentiate IBD subtypes (A mini-review. Can J Gastroenterol Hepatol 2015; 29:157-63). Fecal calprotectin has not proven to be a good measure to distinguish between mild, moderate or severe disease (Inflamm Bowel Dis 2012; 18:1493-7) which is important in deciding appropriate therapeutic intervention. There is a clear need for new approaches that can rapidly and accurately provide an early diagnosis of IBD, particularly considering the lack of good genetic and protein markers, atypical presentations and the often rapid progression of IBD in the pediatric population.

In view of the above there is a need for better diagnostic methods.

SUMMARY

The invention relates to a method for determining a likelihood of presence of IBD disease in a subject comprising the steps of: (A) providing a lower digestive tract biopsy obtained from a subject; B) assessing a level of one or more proteins selected from the group of interferon-induced protein 53, arginosuccinate synthase, Annexin 3, calumenin, Serpin H1, interleukin-25 (IL-25), cytosol aminopeptidase (LAPS; gene name and protein name are used interchangeably herein), Superoxide dismutase, S100A8, S100E, S100A9, visfatin (Nicotinamide phosphoribosyltransferase with uniprot ID P43490), and inorganic pyrophosphatase and combination thereof; C) comparing the level with an average level of the one or more proteins from normal control subjects; wherein a level of the one or more proteins higher than said average level is indicative of disease.

In another aspect there is also provided a method for determining a likelihood of presence of IBD disease in a subject comprising the steps of: A) providing a lower digestive tract biopsy obtained from a subject; B) assessing a level of one or more proteins selected from the group of 3-hydroxy-3 methylglutarate-CoA lyase; amine oxidase A, Aldo-keto reductase family member B10, Macropain delta chain, UDP-glucose 6-dehydrogenase, Iron-sulfur subunit of complex II, Rhodanese, NADH-ubiquinone oxidoreductase 75 kDa subunit, aconitase 2 (mitochondrial), creatinine Kinase B-chain, flavoprotein subunit of complex II, fatty acid binding protein, UDP-glucose 6-dehydrogenase, and leucine-rich PPR motif-containing protein and combination thereof; D) comparing the level with an average level of the one or more proteins from normal control subjects; wherein a level of the one or more proteins lower than the average level is indicative of disease.

In a further aspect there is provided a method for determining a likelihood of presence of IBD disease in a subject comprising determining the likelihood for fatty acid-binding protein, visfatin, UDP-Glucose 6-dehydrogenase, leucine-rich PRR motif-containing protein and inorganic pyrophosphatase according to the above described methods and wherein the disease is present when levels of fatty acid-binding protein, visfatin, UDP-Glucose 6-dehydrogenase, leucine-rich PRR motif-containing protein and inorganic pyrophosphatase are indicative of disease In yet another aspect there is provided a method for determining a likelihood of presence of UC disease in an IBD subject comprising the steps of: A) providing a lower digestive tract biopsy obtained from a subject; B) assessing a level of one or more proteins selected from the group of calumenin, signal recognition particle receptor subunit beta, caldesmon, asparagine synthetase, RING finger protein 71, macropain delta chain, NADH dehydrogenase[ubiquinone] iron sulfur protein 6, cathepsin S, Fibulin-1, Cell death regulatory protein GRIM-19, cavin 1, protein transport protein Sec61 (Sec61; gene name and protein name are used interchangeably herein), Staphylococcal nuclease domain-containing protein 1 (SND1; gene name and protein name are used interchangeably herein), and serotransferrin and combination thereof; C) comparing the level with average levels of said one or more proteins from subjects with CD; wherein a subject with level of said one or more proteins higher than said average levels is indicative of disease.

In another embodiment of the invention there is provided a method for determining a likelihood of presence of UC disease in an IBD subject comprising the steps of: A) providing a lower digestive tract biopsy obtained from a subject; B) assessing a level of one or more proteins selected from the group of carbonate dehydratase II, creatinine kinase B chain, Galectin-3-binding protein and Fatty acid binding protein, trifunctional enzyme subunit beta (mitochondrial), cytosol aminopeptidase, leukotriene A-4 hydrolase, metallothionein-2 (MT2; gene name and protein name are used interchangeably herein), tricarboxylate transport protein (mitochondrial), heterogeneous nuclear ribonucleoprotein H3 (HNRNP H3; gene name and protein name are used interchangeably herein), delta(3,5)-delta(2,4)-dienoyl-CoA isomerase (mitochondrial; ECH1; gene name and protein name are used interchangeably herein), transferrin receptor protein 1, and beta-2-microglobulin and combination thereof; C) comparing the level with average levels of the one or more proteins from subjects with CD; wherein a subject with level of the one or more proteins lower than the average levels is indicative of disease.

There is also provided a method for determining a likelihood of presence of CD disease in an IBD subject comprising the steps of: A) providing a lower digestive tract biopsy obtained from a subject; B) assessing a level of one or more proteins selected from the group of calumenin, signal recognition particle receptor subunit beta, caldesmon, asparagine synthetase, RING finger protein 71, protein transport protein Sec61, Staphylococcal nuclease domain-containing protein 1, and serotransferrin and combination thereof; D) comparing the level with average levels of the one or more proteins from subjects with UC; wherein a subject with level of the one or more proteins lower than the average levels is indicative of disease.

In yet another aspect there is provided a method for determining a likelihood of presence of CD disease in an IBD subject comprising the steps of: A) providing a lower digestive tract biopsy obtained from a subject; B) assessing a level of one or more proteins selected from the group of carbonate dehydratase II, creatinine kinase B chain, Galectin-3-binding pr, Fatty acid binding pr, calcium-activated chloride channel family member 1, Myristoylated alanine-rich C-kinase substrate, uncharacterized protein C19orf21, CD49 antigen-like family member, carbonate dehydratase II, IG mu chain C region, STAT 3, integrin alpha-6, trifunctional enzyme subunit beta (mitochondrial), cytosol aminopeptidase, leukotriene A-4 hydrolase, metallothionein-2, tricarboxylate transport protein (mitochondrial), heterogeneous nuclear ribonucleoprotein H3 (HNRP H3; gene name and protein name are used interchangeably herein), delta(3,5)-delta(2,4)-dienoyl-CoA isomerase (mitochondrial; ECH1), transferrin receptor protein 1, and beta-2-microglobulin and combination thereof; C) comparing the level with average levels of the one or more proteins from normal control subjects and from subjects with UC; wherein a subject with level of the one or more proteins higher than said average levels is indicative of disease.

In another aspect of the invention there is provided a method for diagnosing a severity of IBD, UC or CD disease comprising measuring a level of a biomarker protein for a gut (lower digestive tract) sample, assigning a severity score that correlates with a clinical disease activity index.

In another aspect the method for assessing severity is for CD severity and comprises measuring a level of one or more proteins selected from the proteins listed in column A of table 3, and/or inorganic phosphatase, visfatin, MT2, calumenin, rhodanese, HSP70, Cytochrome c oxidase subunit 5B (COX 5b; gene name and protein name are used interchangeably herein), Cytochrome c oxidase subunit 7C (Cox 7C; gene name and protein name are used interchangeably herein), NADH dehydrogenase [ubiquinone] flavoprotein 1 and flavoprotein subunit of complex II, correlating with PCDAI disease index.

In yet another aspect the method for assessing severity is for UC and comprises measuring a level of one or more proteins selected from the proteins listed in column B of table 3 and/or HNRP H3, Myeloid cell nuclear differentiation Ag, galactowaldenase, carnitine O-palmitoyltransferase 1, Sec 11 and calponin H1, and correlating with PUCAI disease activity.

There is also provided a method for treating IBD, UC or CD in a patient comprising: determining whether said patient has IBD, UC or CD according to any one of or combination of the methods described above and administering to said patient a compound pharmaceutically effective against said IBD, UC or CD.

BRIEF DESCRIPTION OF THE DRAWINGS

The invention will be better understood by way of the following detailed description of embodiments of the invention with reference to the appended drawings, in which:

FIG. 5A-5K are chart of relative ratios of several proteins in control, CD and UC subjects;

FIG. 8 A-E are charts of relative ratios of proteins identified as biomarkers to distinguish UC and CD disease.

FIG. 9 A-D are charts of relative ratios of proteins identified as biomarkers for the severity of UC.

FIG. 14 A-L are charts of relative ratios of proteins identified as biomarkers for distinguishing UC and CD using PLSDA analysis showing high level CD compare to UC.

FIG. 16 A-G are charts of relative ratios of proteins identified as biomarkers for distinguishing control and IBD using PLSDA analysis.

DETAILED DESCRIPTION

Figure 1:
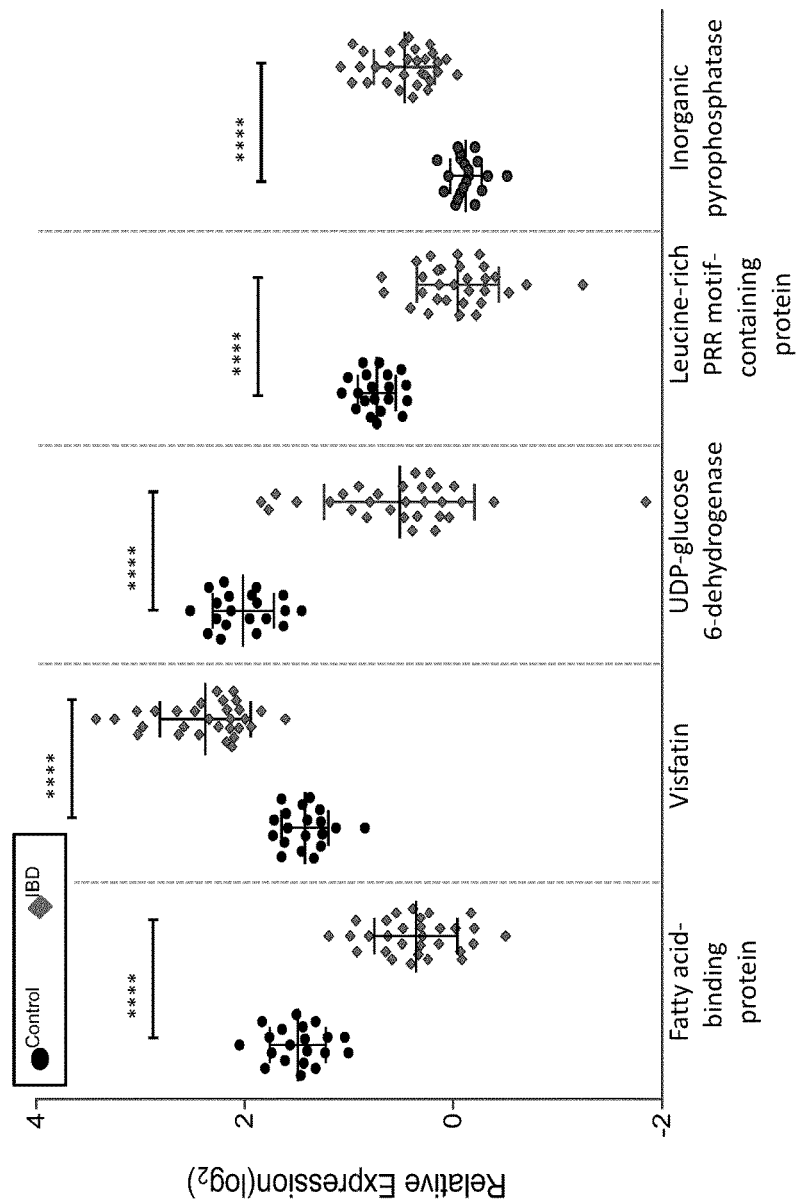
FIG. 1 is a chart of the relative expression of 5 proteins in control and IBD subjects.

The invention will be better understood by way of the following detailed description of embodiments of the invention with reference to the appended drawings and tables.

There is provided proteins markers and methods of using these markers to identify patients with IBD disease as well as to classify IBD disease into underlying conditions (subtypes) namely UC and CD. There is also provided a method for assessing the severity of disease.

By severity of the disease it is meant a level of symptoms as described in disease activity index such Crohn's disease activity index (CDAI), Pediatric Crohn's disease activity index (PCDAI) Harvey-Bradshaw index, Ulcerative colitis activity index (UCAI), Pediatric Ulcerative colitis activity index (PUCAI), Paris classification of pediatric Crohn's disease and the like. For example severe CD corresponds to a score of 450 in the CDAI index.

By patients having Inflammatory Bowel Disease (IBD) it is meant patients with ulcerative colitis (UC) or patients with Crohn's disease (CD) or IBD-undefined (IBD-U).

In one embodiment lower digestive tract biopsies such as colon biopsies were obtained from pediatric patients at the time of diagnostic and prior to therapeutic intervention. Using a super-SILAC-based approach (described further below), the proteomes of non-IBD control, CD, and UC patient biopsies were compared. Biomarker candidates can be identified by classification/regression methods such as Partial Least Squares Discriminant Analyses (PLS-DA), Support Vector Machine (SVM) and Random Forest (RF), ANOVA, t-test, linear regression, and principle component analysis. These methods can be applied to identify proteins that are specific to each disease state. Paired comparisons of proteomes from patient biopsies obtained from non- or inflamed areas of the colon (CoN and CoA respectively) can be employed to identify additional biomarkers of disease severity.

In an aspect of the invention there is provided a method in which IBD can be detected by measuring the levels (or relative abundance) of certain proteins in samples from the gut of patients. Samples from the gut may be obtained from intestinal mucosal biopsies, gut lavage or combination thereof.

In one embodiment of the invention, gut lavage can be performed during endoscopy by flushing a physiological solution, such as sterile saline solution or sterile water, onto the mucosa to remove the strongly adherent mucus layer overlying the intestinal mucosal epithelial cells and the microbial community embedded within the mucus layer. Aspirates are then collected directly through a colonoscope at a specific location in the gut as for example from the terminal ileum, right colon, and left colon and the samples are preferably immediately put on ice right in the endoscopy suite. For example the following steps can be performed: 1) a regular protocol of bowel clean out in preparation for colonoscopy is first applied to the patient, 2) then the colonoscope ("scope") is advanced to the ascending colon or a region of the colon distal to that of interest, 3) suction out fluid and particulate matter, using either the scope's wash system or with a syringe through biopsy port, 4) flush sterile water onto mucosa until shards of mucus are dislodged, 5) aspirate mucus containing fluid into sterile trap through scope aspiration system, 6) remove the trap from scope suction and cap it and immediately place on ice, 7) advance the scope to more proximal region of interest and repeat steps 3-6, 8) traps with mucus are placed on ice until further processing. The sample can then be analyzed at the point of care or transferred to a laboratory. The samples can also be further processed and then stored at −80° C.

Biopsies can be obtained by procedures that are well known in the art and can be obtained from region of the colon that are macroscopically inflamed or not.

Proteins can be indentified and quantified by techniques known in the art such as shotgun mass-spectrometry in conjunction with protein fractionation. Other method for detecting specific proteins such as, immunology based methods (antibodies), western blots, spectrophotometry, enzyme assays, ELISA and any other method as would be known to one skilled in the art may also be used.

Analysis of the data can be performed using for example proteomic software packages such as the MaxQuant software and using software such as, but not limited to, Perseus, matlab, Roccet and R for validation and statistical analysis.

In one embodiment of the invention, the presence of IBD disease in a subject can be assessed by the relative abundance of certain host proteins. In this respect it is shown that certain proteins exhibit a difference in their relative abundance in individuals with UC or CD disease relative to healthy (IBD-free, also referred to as controls) individuals and therefore indicate the presence of IBD.

In another embodiment of the invention CD and UC disease can be distinguished in IBD patients by determining the relative abundance of certain host proteins. In this respect, it is shown that certain proteins exhibit a difference in their relative abundance in individuals with UC vs individuals with CD and therefore these proteins can be used as markers to distinguish between CD and UC.

In yet another embodiment of the invention the severity of UC disease can be assessed by the relative abundance of certain host proteins. In this respect it is shown that certain proteins exhibit a difference in their relative abundance with respect to controls in individuals with mild, moderate or severe UC disease.

The invention provides a method in which the severity of CD disease can be assessed by the relative abundance of certain host proteins. In this respect it is shown that certain proteins exhibit a difference in their relative abundance with respect to controls in individuals with mild, moderate or severe CD disease.

It will be appreciated that a subject's diagnosis can be achieved by measuring the levels of one or more protein markers and by comparing these levels to average levels of the one or more markers in controls and/or disease groups that have been previously acquired and analyzed. It will be further appreciated that several markers may be combined for example to increase the statistical significance or accuracy or the diagnosis or to reduce the number of false positives or false negatives and the like. Furthermore it will be appreciated that ratios of relative abundance between markers can also be derived that are indicative of presence, type and severity of disease.

The differences in the relative abundance of proteins in individuals were assessed using different statistical models. It will be appreciated that the choice of an appropriate statistical model may depend on the size of the samples, distributions of experimental values, the outcome being tested and any other factors affecting the relevance of a particular model. It will further be appreciated that certain protein markers may be identified as such by a certain statistical model but not another. In other words certain statistical models may have sufficient discrimination power while others may not. Furthermore within a same model discrimination power may vary depending on the test parameters.

There is also provided a method for assessing the severity of the disease by measuring an amount or a relative amount of one or more proteins to provide a clinical index correlation number. The present invention established that the abundance or relative abundance of certain proteins correlate with the severity of disease, in particular UC or CD disease as determined by clinical disease activity indexes such as PUCAI or PCDAI. Therefore this correlation enables the establishment of a clinical correlation index number using the measured abundance or relative abundance of certain proteins as will be further described below.

The above methods for identifying IBD, UC and CD disease, or the severity of the disease enable the establishment of more specific, timely and efficient treatment protocols for patients. The treatment protocols are well known by health professionals when the diagnosis is established. However, as mentioned above such diagnoses are sometimes difficult to make. The methods described above to establish diagnosis can therefore be advantageously relied on to determine appropriate treatment protocols.

IBD in general and UC and CD disease can be treated using pharmaceutically acceptable amounts of one or more compounds selected for example from the group of aminosalycylates, immunomodulators, anti-integrins, anti-cytokines, enteral feed programs, steroids, corticosteroids, antibiotics, anti-TNFa, bismuth or a combination thereof.

However, knowing the type, stage and severity of the disease is crucial in determining the optimal treatment. For example, mild UC may benefit from aminosalicylates treatment while severe UC may be more responsive to immunomodulators.

EXAMPLES

Example 1

Material and Methods
Subjects Selection and Sampling:
All patients under 18 years of age and scheduled to undergo diagnostic colonoscopy were considered eligible for recruitment. Exclusion criteria, related to conditions known to affect mucosal gene expression, included: (1) a body mass index greater than the 95$^{th}$ percentile for age; (2) diabetes mellitus (insulin and non-insulin dependent); (3) infectious gastroenteritis within the preceding 2 months; (4) use of any antibiotics or probiotics within the last 4 weeks; or (5) IBS. These same exclusion criteria were applied to the non-IBD control group. All IBD cases met the standard diagnostic criteria for either ulcerative colitis (UC) or Crohn's disease (CD) following thorough clinical, microbiologic, endoscopic, histologic and radiologic evaluation (J Pediatr Gastroenterol Nutr 2007; 44:653-74). Phenotyping of disease was based on endoscopy and clinical disease activity scores and recorded utilizing the Paris modification of the Montreal Classification for IBD (Inflamm Bowel Dis 2011; 17:1314-21). Clinical disease activity of CD was determined using the Pediatric Crohn's Disease Activity Index (PCDAI)(J Pediatr Gastroenterol Nutr 2005; 41:416-21) and of UC using the Pediatric Ulcerative Colitis Activity Index (PUCAI)(Gastroenterology 2007; 133:423-32). All controls had a macroscopically and histologically normal mucosa, and did not carry a diagnosis for any known chronic intestinal disorder (e.g. celiac disease, eosinophilic enterocolitis, IBS). Ascending colon and terminal ileum is the most common site of CD, and pancolitis is common in children with UC (Isr Med Assoc J 2000; 2:598-600); the ascending colon was chosen as the site for mucosal biopsy to eliminate the region of the bowel biopsied as a confounder. As such, only patients from whom ascending colon biopsies were obtained were included in the proteomic study.

The study was approved by the Research Ethics Board of the Children's Hospital of Eastern Ontario (CHEO). Subject clinical data were collected and managed using Research Electronic Data Capture (REDCap) (J Biomed Inform 2009; 42:377-81) hosted at the CHEO Research Institute.

Sample Processing and Analyses:

Briefly, frozen biopsies were lysed by mechanical homogenization and proteins isolated following centrifugation. 45 µg of sample protein was combined with an equal amount of isotopically-labeled reference protein lysate to permit for relative quantification of proteins. Tryptic digestion of proteins were performed with filter-aided sample preparation (Nat Methods 2009; 6:359-62.), and resulting peptides analyzed on an Orbitrap Elite mass spectrometer (MS). All MS raw files were analyzed in a single run with MaxQuant version 1.5.1, against the human Uniprot database (Version Human_20140711). Data filtering and statistical analysis were performed in Perseus, Excel (Microsoft), and Prism (Graphpad).

Mathematical models of the classification of disease states were developed with a proteomic data from a subset of the patients (discovery cohort), and the models substantiated with data from the remaining patients (validation cohort). Patient biopsies were randomly divided into equal groups between the discovery and the validation cohorts using a balanced stratification approach for gender and diagnosis (Etcetera in WinPepi, BixtonHealth.ca). Candidate biomarker selection was performed by Partial Least Squares Discriminant Analyses (PLS-DA), Support Vector Machine (SVM) and Random Forest (RF) on the discovery cohort dataset with ROC Curve Explorer and Tester (ROCCET) (Metabolomics 2013; 9:280-299). For each model, the performance was tested with repeated random sub-sampling cross validation wherein ⅔ of the samples where used for training and ⅓ for testing, with 50 permutations. Ultimately, the candidate biomarkers that were selected were identified as significant in all three models, and ranked by the Area Under the Receiver Operator Curve (AUROC) value. Candidate biomarker panels were developed in the ROC Curve Tester module of ROCCET by iterative analysis with a PLSDA model using a step-forward method, with candidate biomarkers added by protein-specific AUROC values. The minimal number of proteins selected for inclusion in the panel was based upon the point of plateau for the ROC AUC, specificity and sensitivity. Biomarker panels were independently validated by applying the validation cohort data to the discovery-trained PLSDA models.

The discovery cohort PCDAI or PUCDAI scores for CD and UC, respectively, were compared with all proteins in the Q95+ subgroup specific proteins to determine the Pearson correlation (Graphpad, Prism). Pathway analyses were performed using Panther (Pantherdb.org) and visualized with iPATH2 interactive pathways explorer (pathways.embl.de) using uniprot accession numbers. Enzyme linked immunosorbent assays (ELISAs) for visfatin (Ezno Life Sciences, NY, USA) and metallothionein-2 (Cloud-Clone Corp., TX, USA) were performed as per the manufacturers protocol on biopsy lysate diluted to a final SDS concentration of 0.08%.

Results

Subjects

Children undergoing diagnostic colonoscopy were recruited for this proteomic study. Briefly, over the course of 3 years, ascending colon biopsies were obtained from 101 patients that met the study criteria. The mean age of IBD patients was 13.6±0.4 years (n=61, range 4.8-17.8), and of the controls was 14.4±0.5 years (n=40, range 6.1-17.7), and were comparable between groups. No gender bias was observed within control or UC patients. A greater percentage of male CD patients than females were recruited. This gender bias is characteristic for CD in pediatric populations (Nat Rev Gastroenterol Hepatol 2014; 11:88-98). The majority of CD patients (83.3%) had active inflammatory colonic/ileocolonic disease; 86.7% of UC patients exhibited pancolitis.

Evaluation of Full Proteomic Data Set:

101 biopsies were processed over a 15-month period and analyzed by HPLC-ESI-MSMS to identify and quantify proteins that are differentially expressed between disease conditions. One biopsy was rejected from the analysis. The remaining samples showed consistent MS profiles over time.

From the 100 remaining patient biopsies included for analyses, 3583 proteins were identified by ≥2 unique peptides, 948 of which were quantified in ≥95% of the biopsies (Q95). There were 66 proteins considered to be subgroup specific due to the overrepresentation in one subgroup (>70% of subgroup biopsies) when compared with at least one other subgroup (<50% of subgroup biopsies). Principal component analysis (PCA) was performed to test whether the proteomics results could segregate patients with different disease status. To limit the effects due to imputation of missing data, only the data from the Q95 and the subgroup specific proteins were used. Using these 1014 proteins, control and IBD proteomes are distinguished by PCA. Interestingly, group segregation was also obtained even when proteins annotated as involved in immunological response were removed from the dataset. Consistent with previous studies, blood based parameters (Hemoglobin, Albumin, C-reative protein (CRP), erythrocyte sedimentation rate (ESR)) were insufficient to segregate patients by PCA analysis.

Establishment of Biomarker Models:

Control Vs. IBD

To determine the minimal subset of proteins that can segregate IBD from control patients, analysis was performed on the discovery cohort with ROC Curve Explorer and Tester (ROCCET)(Metabolomics 2013; 9:280-299). Briefly, control proteomes were compared with IBD (combined CD and UC) proteomes in the multivariate ROC curve explorer module (Metabolomics 2013; 9:280-299) using SVM, PLSDA and RF. There were 106 proteins common to all three models (Table 1).

TABLE 1

ATP-binding cassette sub-family D member 3
6-phosphogluconate dehydrogenase, decarboxylating
Nicotinamide phosphoribosyltransferase
Heat shock 70 kDa protein 1A/1B
Deleted in malignant brain tumors 1 protein
Phosphatidylethanolamine-binding protein 1; Hippocampal cholinergic neurostimulating peptide
Protein ERGIC-53
Peroxiredoxin-4
ATP synthase protein 8
Glycogen phosphorylase, brain form
Thioredoxin domain-containing protein 5
Acetyl-CoA acetyltransferase, mitochondrial
Trifunctional enzyme subunit beta, mitochondrial; 3-ketoacyl-CoA thiolase
Plastin-1
Protein S100-A11; Protein S100-A11, N-terminally processed
Villin-1
Cytoskeleton-associated protein 4
Cytochrome b-c1 complex subunit 6, mitochondrial
Calponin-2
Lactotransferrin; Lactoferricin-H; Kaliocin-1; Lactoferroxin-A; Lactoferroxin-B; Lactoferroxin-C
Thiosulfate sulfurtransferase
Neutrophil elastase
Cytochrome c oxidase subunit 6C
Unconventional myosin-Id
Gamma-interferon-inducible protein 16
Normal mucosa of esophagus-specific gene 1 protein
Four and a half LIM domains protein 1
Major vault protein
Fumarate hydratase, mitochondrial
Serpin H1
Filamin-B
78 kDa glucose-regulated protein
N(G),N(G)-dimethylarginine dimethylaminohydrolase 1
Proteasome activator complex subunit 1
Phosphoserine aminotransferase
Nucleobindin-2; Nesfatin-1
Creatine kinase B-type
Selenium-binding protein 1
SWI/SNF-related matrix-associated actin-dependent regulator of chromatin subfamily A member 5
Mesencephalic astrocyte-derived neurotrophic factor
Calreticulin
Protein S100-P
SRA stem-loop-interacting RNA-binding protein, mitochondrial
Electron transfer flavoprotein subunit beta
Polymerase I and transcript release factor
Ig kappa chain C region
Superoxide dismutase [Mn], mitochondrial
Cytosol aminopeptidase
Epithelial cell adhesion molecule
7-dehydrocholesterol reductase
2,4-dienoyl-CoA reductase, mitochondrial
Adenosylhomocysteinase; Putative adenosylhomocysteinase 3
Protein disulfide-isomerase
Lithostathine-1-alpha
Guanine nucleotide-binding protein G(I)/G(S)/G(O) subunit gamma-5
Endoplasmin
Fatty acid-binding protein, epidermal
Plastin-3
Cytochrome b-c1 complex subunit 7
Succinate dehydrogenase [ubiquinone] iron-sulfur subunit, mitochondrial
Aconitate hydratase, mitochondrial
Myeloid cell nuclear differentiation antigen
Inorganic pyrophosphatase
HLA class I histocompatibility antigen, A-24 alpha chain
Creatine kinase U-type, mitochondrial
Succinyl-CoA ligase [ADP-forming] subunit beta, mitochondrial
Carboxypeptidase; Lysosomal protective protein; Lysosomal protective protein 32 kDa chain; Lysosomal protective protein 20 kDa chain
Annexin A3; Annexin
Transmembrane emp24 domain-containing protein 9
Very long-chain specific acyl-CoA dehydrogenase, mitochondrial
Galectin-4; Galectin
NAD-dependent malic enzyme, mitochondrial
Protein NipSnap homolog 1
Vigilin
3-ketoacyl-CoA thiolase, mitochondrial
Acyl-CoA synthetase family member 2, mitochondrial

TABLE 1-continued

Ig gamma-1 chain C region
Proteasome subunit beta type-6
CD9 antigen
NADH dehydrogenase [ubiquinone] 1 alpha subcomplex subunit 13
Leucine-rich PPR motif-containing protein, mitochondrial
Histone H1.0; Histone H1.0, N-terminally processed
UDP-glucose 6-dehydrogenase
Electron transfer flavoprotein subunit alpha, mitochondrial
Beta-2-microglobulin; Beta-2-microglobulin form pI 5.3
Integrin beta-2; Integrin beta
Zyxin
Succinate dehydrogenase [ubiquinone] flavoprotein subunit, mitochondrial
Basigin
Carbonyl reductase [NADPH] 1
Calpastatin
Estradiol 17-beta-dehydrogenase 2
Alpha-2-macroglobulin
CD44 antigen
Proteasome activator complex subunit 2
Junction plakoglobin
Cell surface A33 antigen
Transgelin
Keratin, type I cytoskeletal 18
Retinal dehydrogenase 1
Cathepsin Z
Alcohol dehydrogenase 1C
Mucin-2
Chloride anion exchanger
Tryptophan--tRNA ligase, cytoplasmic; T1-TrpRS; T2-TrpRS
Vesicular integral-membrane protein VIP36

To identify the minimal number and the particular proteins required for control vs IBD segregation, a PLSDA model was evaluated in the Tester module of ROCCET. By step-forward analysis, a peak and stabilization of the AUC, specificity and sensitivity was observed with five proteins. The relative expressions of these 5 proteins is shown in FIG. 1, was sufficient to differentiate IBD patients from controls with an AUC of 1.0 (95% Cl 1.0-1.0), and a classification accuracy of 94.5%.

CD Vs. UC

From the 15 CD and 15 UC proteomes included in the discovery cohort for sub-classification, a total of 956 from the 1024 possible proteins were identified, though just over 26% (252) were common to the three models employed, namely SVM, PLSDA and RF (table 2).

TABLE 2

Protein transport protein Sec61 subunit alpha isoform 1
Cytosol aminopeptidase
Staphylococcal nuclease domain-containing protein 1
Leukotriene A-4 hydrolase
Trifunctional enzyme subunit beta, mitochondrial; 3-ketoacyl-CoA thiolase
Metallothionein-2
Peroxiredoxin-5, mitochondrial
ATP synthase subunit beta, mitochondrial; ATP synthase subunit beta
Heterogeneous nuclear ribonucleoprotein H3
Thymosin beta-10
Heat shock 70 kDa protein 1A/1B
Serotransferrin
Delta(3,5)-Delta(2,4)-dienoyl-CoA isomerase, mitochondrial
Tricarboxylate transport protein, mitochondrial
Aminopeptidase B
Tryptophan--tRNA ligase, cytoplasmic; T1-TrpRS; T2-TrpRS
Transferrin receptor protein 1; Transferrin receptor protein 1, serum form
3-beta-hydroxysteroid-Delta(8),Delta(7)-isomerase
Vigilin
Proto-oncogene tyrosine-protein kinase Src
Filamin-C
Histone H1.0; Histone H1.0, N-terminally processed
S-formylglutathione hydrolase
Translocon-associated protein subunit delta
Neuroblast differentiation-associated protein AHNAK
Calumenin TABLE 2-continued Ras-related protein Rab-1B
NADH dehydrogenase [ubiquinone] iron-sulfur protein 2, mitochondrial
Acyl-CoA-binding protein
6-phosphogluconolactonase
Hypoxia up-regulated protein 1
Fibrinogen alpha chain; Fibrinopeptide A; Fibrinogen alpha chain
Protein kinase C and casein kinase substrate in neurons protein 2
Bone marrow proteoglycan; Eosinophil granule major basic protein
Beta-2-microglobulin; Beta-2-microglobulin form pI 5.3
Glutathione reductase, mitochondrial
Coronin-1B; Coronin
Guanine nucleotide-binding protein G(I)/G(S)/G(O) subunit gamma-5
Vacuolar protein sorting-associated protein 29
Palladin
Aconitate hydratase, mitochondrial
Myristoylated alanine-rich C-kinase substrate
ATP synthase subunit d, mitochondrial
U1 small nuclear ribonucleoprotein A
Eosinophil cationic protein
Fatty acid-binding protein, epidermal
Signal transducer and activator of transcription 1-alpha/beta; Signal transducer and activator of transcription
Flavin reductase (NADPH)
Calcyclin-binding protein
Creatine kinase B-type
ATP synthase subunit epsilon, mitochondrial; ATP synthase subunit epsilon-like protein, mitochondrial
OCIA domain-containing protein 2
Actin-related protein 2/3 complex subunit 5
Dihydropteridine reductase
Programmed cell death protein 5
Protein canopy homolog 2
Glycerol-3-phosphate dehydrogenase, mitochondrial
Sorting nexin-3
Aldo-keto reductase family 1 member C3
Vinculin
Cysteine and glycine-rich protein 1
Histone H1x
Extended synaptotagmin-1
Aflatoxin B1 aldehyde reductase member 2
Transmembrane emp24 domain-containing protein 9
Signal recognition particle subunit SRP72
Ig gamma-3 chain C region
Desmin
Spermidine synthase
Nicotinamide phosphoribosyltransferase
Tropomyosin alpha-4 chain
Laminin subunit gamma-1
Integrin-linked protein kinase
Destrin
2,4-dienoyl-CoA reductase, mitochondrial
Endothelial differentiation-related factor 1
Medium-chain specific acyl-CoA dehydrogenase, mitochondrial
Acyl-protein thioesterase 1
Protein transport protein Sec23B
Filamin-A
Microtubule-associated protein; Microtubule-associated protein 4
PC4 and SFRS1-interacting protein
7-dehydrocholesterol reductase
Signal peptidase complex subunit 2
Myosin light chain kinase, smooth muscle; Myosin light chain kinase, smooth muscle, deglutamylated form
Transforming growth factor-beta-induced protein ig-h3
NAD(P) transhydrogenase, mitochondrial
Cathepsin B; Cathepsin B light chain; Cathepsin B heavy chain
Hydroxyacyl-coenzyme A dehydrogenase, mitochondrial
Amine oxidase [flavin-containing] A
Spermine synthase
Histone H1.4
Nck-associated protein 1
DNA replication licensing factor MCM7
Glutaredoxin-1
Cytochrome c oxidase subunit 4 isoform 1, mitochondrial
Integrin beta-4
PDZ and LIM domain protein 1
Myosin light chain 1/3, skeletal muscle isoform; Myosin light chain 3
Carboxypeptidase; Lysosomal protective protein; Lysosomal protective protein 32 kDa chain; Lysosomal protective protein 20 kDa chain
ERO1-like protein alpha
V-type proton ATPase subunit E 1

TABLE 2-continued

CD44 antigen
Ribosomal L1 domain-containing protein 1
Basement membrane-specific heparan sulfate proteoglycan core protein; Endorepellin; LG3 peptide
Tryptase alpha/beta-1; Tryptase beta-2
Copine-1
Peptidyl-prolyl cis-trans isomerase FKBP2; Peptidyl-prolyl cis-trans isomerase
DnaJ homolog subfamily B member 1
Collagen alpha-2(VI) chain
Rho-associated protein kinase 2
Dihydrolipoyllysine-residue succinyltransferase component of 2-oxoglutarate dehydrogenase complex, mitochondrial
Mitochondrial-processing peptidase subunit beta
Myosin-11
Replication protein A 32 kDa subunit
Four and a half LIM domains protein 2
Aldehyde dehydrogenase, mitochondrial
NADH-ubiquinone oxidoreductase 75 kDa subunit, mitochondrial
Unconventional myosin-Ib
Zyxin
Junction plakoglobin
IgGFc-binding protein
Ig alpha-1 chain C region
Argininosuccinate synthase
Dipeptidyl peptidase 3
Tropomodulin-3
Myosin regulatory light chain 12A; Myosin regulatory light chain 12B
NADH dehydrogenase [ubiquinone] 1 beta subcomplex subunit 4
Ribosome maturation protein SBDS
Proteasome subunit beta type-8
Superoxide dismutase [Mn], mitochondrial
HLA class I histocompatibility antigen, A-24 alpha chain
Protein S100-P
Coactosin-like protein
Serine/arginine repetitive matrix protein 2
SH3 domain-binding glutamic acid-rich-like protein
Vesicle-trafficking protein SEC22b
NEDD8-conjugating enzyme Ubc12
Succinate dehydrogenase [ubiquinone] iron-sulfur subunit, mitochondrial
Desmoplakin
Succinyl-CoA: 3-ketoacid coenzyme A transferase 1, mitochondrial
Fibrinogen beta chain; Fibrinopeptide B; Fibrinogen beta chain
Actin-related protein 2/3 complex subunit 3
Protein-glutamine gamma-glutamyltransferase 2
Sulfide: quinone oxidoreductase, mitochondrial
Haptoglobin; Haptoglobin alpha chain; Haptoglobin beta chain
Pyruvate carboxylase, mitochondrial
N(G),N(G)-dimethylarginine dimethylaminohydrolase 2
Creatine kinase U-type, mitochondrial
Polymerase I and transcript release factor
Epididymal secretory protein E1
Alpha-2-macroglobulin
Transmembrane emp24 domain-containing protein 7
Fibrillin-1
Phosphoserine aminotransferase
Purine nucleoside phosphorylase
SUMO-activating enzyme subunit 2
Cytoplasmic aconitate hydratase
Transcription factor A, mitochondrial
Isovaleryl-CoA dehydrogenase, mitochondrial
Protein S100-A8; Protein S100-A8, N-terminally processed
Deoxyuridine 5-triphosphate nucleotidohydrolase, mitochondrial
Protein CDV3 homolog
Zymogen granule membrane protein 16
Four and a half LIM domains protein 1
Polymeric immunoglobulin receptor; Secretory component
Hydroxymethylglutaryl-CoA synthase, cytoplasmic
Fascin
Ras-related protein Rab-2A
Moesin
Prelamin-A/C; Lamin-A/C
Ig gamma-1 chain C region
Galectin-3; Galectin
Heterogeneous nuclear ribonucleoprotein U-like protein 1
Caldesmon
NADH dehydrogenase [ubiquinone] 1 alpha subcomplex subunit 13
Aminopeptidase N
Cytochrome b-c1 complex subunit 8
Galectin-4; Galectin TABLE 2-continued Aldo-keto reductase family 1 member B10
N(G),N(G)-dimethylarginine dimethylaminohydrolase 1
Histone H1.3
N-alpha-acetyltransferase 15, NatA auxiliary subunit
Plastin-1
Complement C3; Complement C3 beta chain; C3-beta-c; Complement C3 alpha chain; C3a anaphylatoxin; Acylation stimulating protein; Complement C3b alpha chain; Complement C3c alpha chain fragment 1; Complement C3dg fragment; Complement C3c fragment; Complement C3d fragment; Complement C3f fragment; Complement C3c alpha chain fragment 2
Cyclin-dependent kinase 1
Adenosylhomocysteinase; Putative adenosylhomocysteinase 3
Estradiol 17-beta-dehydrogenase 11
Plastin-3
3-ketoacyl-CoA thiolase, mitochondrial
Glutathione S-transferase kappa 1
Prosaposin; Saposin-A; Saposin-B-Val; Saposin-B; Saposin-C; Saposin-D
Receptor expression-enhancing protein 5
Leukocyte elastase inhibitor
Probable ATP-dependent RNA helicase DDX46
Collagen alpha-2(I) chain
cAMP-dependent protein kinase type II-alpha regulatory subunit
Metastasis-associated protein MTA2
Bifunctional 3-phosphoadenosine 5-phosphosulfate synthase 2; Sulfate adenylyltransferase; Adenylyl-sulfate kinase
Deoxynucleoside triphosphate triphosphohydrolase SAMHD1
Ornithine aminotransferase, mitochondrial; Ornithine aminotransferase, hepatic form; Ornithine aminotransferase, renal form
Cathepsin G
Desmoglein-2
DNA replication licensing factor MCM4
Selenium-binding protein 1
Alcohol dehydrogenase 1C
Transmembrane protein 109
Thymosin beta-4; Hematopoietic system regulatory peptide
Magnesium transporter protein 1
Ig lambda-2 chain C regions
Nuclear pore complex protein Nup205
GDP-mannose 4,6 dehydratase
Hemoglobin subunit delta
Caspase; Caspase-1; Caspase-1 subunit p20; Caspase-1 subunit p10
UPF0556 protein C19orf10
UDP-glucose: glycoprotein glucosyltransferase 1
Apolipoprotein A-I; Proapolipoprotein A-I; Truncated apolipoprotein A-I
Eosinophil peroxidase; Eosinophil peroxidase light chain; Eosinophil peroxidase heavy chain
Coronin-1A; Coronin
Quinone oxidoreductase
Protein S100-A9
Hemoglobin subunit alpha
Serpin B6
Immunoglobulin J chain
Calpastatin
CD59 glycoprotein
Thymidine phosphorylase
Nuclear ubiquitous casein and cyclin-dependent kinase substrate 1
Alpha-1-antitrypsin; Short peptide from AAT
Granulins; Acrogranin; Paragranulin; Granulin-1; Granulin-2; Granulin-3; Granulin-4; Granulin-5; Granulin-6; Granulin-7
Anterior gradient protein 2 homolog
Dolichyl-diphosphooligosaccharide--protein glycosyltransferase subunit STT3B
Transgelin
Macrophage-capping protein
Myosin-14
Tubulin alpha-4A chain
Collagen alpha-1(VI) chain
Serpin H1
Mucin-2
D-3-phosphoglycerate dehydrogenase
Unconventional myosin-Id
Cystatin-B
Nucleolar RNA helicase 2
RNA-binding protein 39
Neutrophil defensin 3; HP 3-56; Neutrophil defensin 2
Succinyl-CoA ligase [GDP-forming] subunit beta, mitochondrial
ADP/ATP translocase 3; ADP/ATP translocase 3, N-terminally processed
Vasodilator-stimulated phosphoprotein
Calcium-activated chloride channel regulator 1

TABLE 2-continued

Fibrinogen gamma chain
Probable ATP-dependent RNA helicase DDX23

Figure 2:
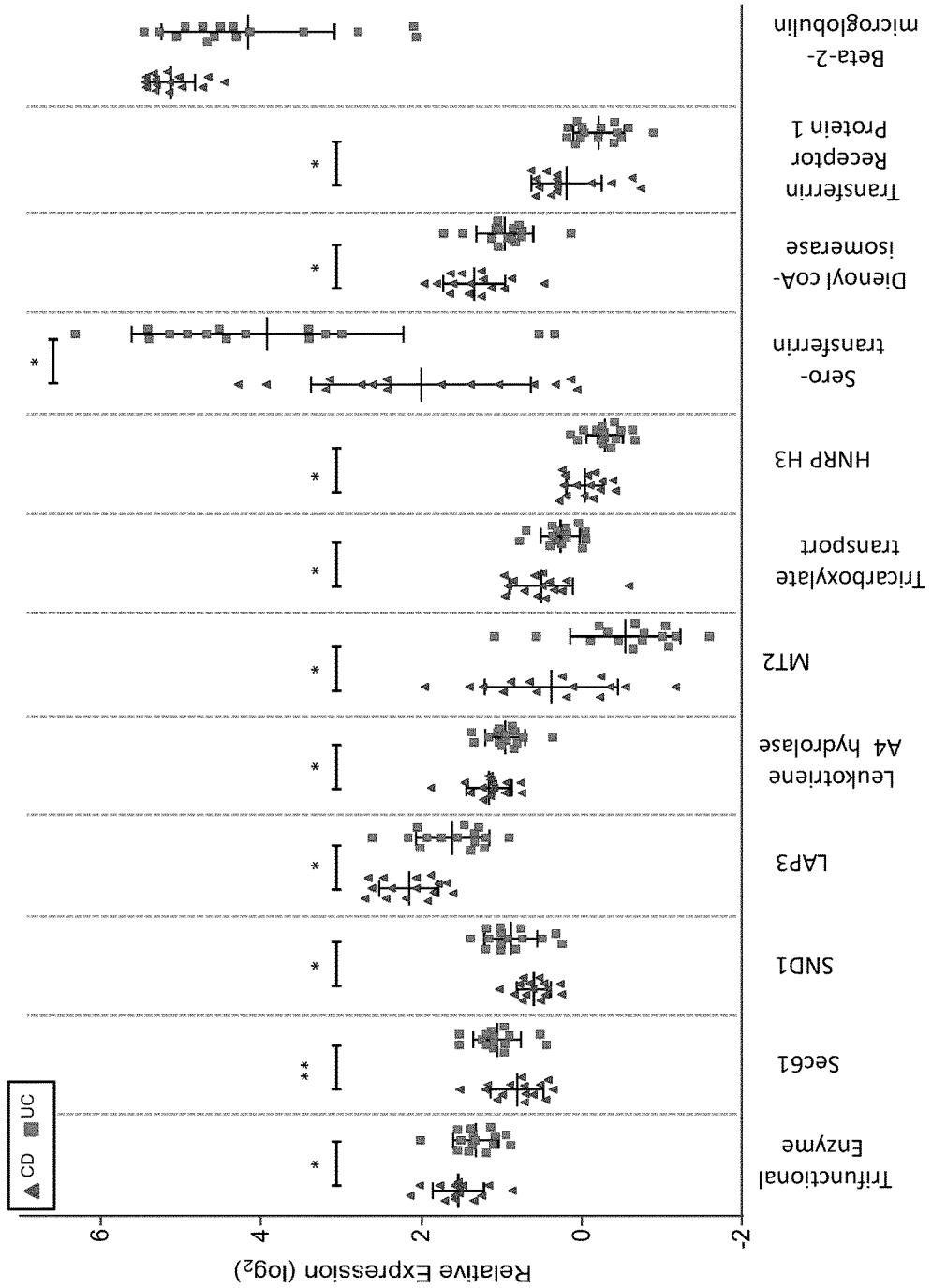
FIG. 2 is a chart of the relative expression of 12 proteins in CD and UC subjects.

Step forward analysis of the 252 proteins was applied to the PLSDA model to identify the minimal number and candidate biomarker proteins required for segregation of CD from UC. Points of inflection were observed in the AUC with 3, 5, 8, and 10 proteins. A plateau in specificity and sensitivity was observed at 12 proteins, and thus determined to be the minimal number of proteins required for optimal classification. The relative expression of the 12 proteins is shown (FIG. 2). Notably, beta-2-microglobulin was not significantly different between CD and UC groups after FDR adjustment (p=0.0703), though contributes to the specificity and sensitivity of the panel (FIG. 1D). The panel of 12 proteins resulted in an overall AUC of 0.958 (95% CI 0.84-1.0), with a sensitivity and specificity of 1.0 and 0.933 respectively.

Application and performance evaluation of the panels to an independent validation cohort:

As outlined, independent validation of the biomarker panels PLSDA models were accomplished by assessment of the proteomic data from the validation cohort. Proteins of FIG. 1 applied to the classification of the validation cohort result in an AUC of 0.997, with 48/50 patients accurately classified as either control or IBD as determined by ROC analysis. Similarly, the 12 proteins of FIG. 2 differentiate CD from UC with an AUC of 0.862, with 24 of 30 patients accurately classified. PCA performed using the proteins of FIG. 2 shows good separation of the CD and UC populations. Despite reduced sensitivity and specificity in the validation cohort compared with the discovery group, these results indicate the utility of the biomarker panels in diagnosis and sub-diagnosis of IBD patients.

Candidate Biomarkers are Biologically Relevant.

Pathway analysis was performed to evaluate the functional roles of the 106 IBD and 252 differential diagnostic candidate biomarkers. The majority of proteins that segregate IBD from control are involved in metabolic processes, and function predominantly in catalysis, specifically oxidoreductase activity. Canonical pathways identified to differ in IBD are related to energy metabolism. Proteins elevated in CD are related to fatty acid metabolism whereas proteins elevated in UC function in energy metabolism.

Correlation with Severity:

Pearson correlation was calculated on the 945 Q95+ subgroup specific proteins in the discovery cohort with the severity of the disease based on the PCDAI/PUCAI patient scores. In total, 118 proteins correlated significantly with PCDAI or PUCAI (table 3).

TABLE 3

| Correlation with CD severity; Column A | Correlation with UC severity; Column B |
|---|---|
| Inorganic pyrophosphatase | Caldesmon |
| Caldesmon | Heterogeneous nuclear ribonucleoprotein U-like protein 2 |
| Heterogeneous nuclear ribonucleoprotein U-like protein 2 | Integrin-linked protein kinase |
| Integrin-linked protein kinase | Ras-related protein Rab-18 |
| Ras-related protein Rab-18 | RNA-binding protein 3 |
| RNA-binding protein 3 | Annexin A3 |
| 14-3-3 protein eta | Eosinophil peroxidase |
| 26S protease regulatory subunit 8 | Nuclear ubiquitous casein and cyclin-dependent kinase substrate 1 |

TABLE 3-continued

| Correlation with CD severity; Column A | Correlation with UC severity; Column B |
|---|---|
| 4-trimethylaminobutyraldehyde dehydrogenase | Heterogeneous nuclear ribonucleoprotein H3 |
| 60S ribosomal protein L29 | 116 kDa U5 small nuclear ribonucleoprotein component |
| 60S ribosomal protein L35a | 40S ribosomal protein S28 |
| 6-phosphogluconolactonase | Aconitate hydratase, mitochondrial |
| 78 kDa glucose-regulated protein | Antigen peptide transporter 1 |
| Adipocyte plasma membrane-associated protein | Coronin-1C |
| Alpha-aminoadipic semialdehyde dehydrogenase | Eukaryotic translation initiation factor 3 subunit A |
| Apolipoprotein A-I | Eukaryotic translation initiation factor 3 subunit E |
| Calnexin | Eukaryotic translation initiation factor 4B |
| Calreticulin | Fibrinogen alpha chain |
| Cellular nucleic acid-binding protein | Galectin-3 |
| Chloride intracellular channel protein 1 | Haptoglobin |
| Cleavage and polyadenylation specificity factor subunit 5 | Heterogeneous nuclear ribonucleoprotein L |
| Collagen alpha-2(VI) chain | Heterogeneous nuclear ribonucleoproteins A2/B1 |
| Coronin-1A | Hypoxanthine-guanine phosphoribosyltransferase |
| Cytochrome c oxidase subunit 5A, mitochondrial | KH domain-containing, RNA-binding, signal transduction-associated protein 1 |
| Eukaryotic translation initiation factor 2 subunit 1 | Laminin subunit gamma-1 |
| Eukaryotic translation initiation factor 4H | Leukocyte elastase inhibitor |
| FACT complex subunit SPT16 | LIM and SH3 domain protein 1 |
| Filamin-C | Myeloid cell nuclear differentiation antigen |
| Four and a half LIM domains protein 1 | Myosin regulatory light chain 12A |
| Heat shock protein 105 kDa | Non-POU domain-containing octamer-binding protein |
| Heterogeneous nuclear ribonucleoprotein A0 | Nucleolin |
| Lactotransferrin | Obg-like ATPase 1 |
| Lamina-associated polypeptide 2, isoforms beta/gamma | Protein transport protein Sec23A |
| Matrin-3 | Protein-L-isoaspartate O-methyltransferase |
| Moesin | Puromycin-sensitive aminopeptidase |
| Nucleolar and coiled-body phosphoprotein 1 | rRNA 2'-O-methyltransferase fibrillarin |
| Nucleolysin TIAR | Serine/arginine-rich-splicing factor 7 |
| PDZ and LIM domain protein 5 | Signal recognition particle 9 kDa protein |
| Peptidyl-prolyl cis-trans isomerase FKBP4 | Small nuclear ribonucleoprotein-associated proteins B and B' |
| Perilipin-3 | Splicing factor 3A subunit 3 |
| Phosphatidylethanolamine-binding protein 1 | T-complex protein 1 subunit beta |
| Prelamin-A/C | Thyroid hormone receptor-associated protein 3 |
| Protein canopy homolog 2 | Transportin-1 |
| Protein NipSnap homolog 1 | |
| Protein phosphatase 1G | |
| Protein transport protein Sec61 subunit beta | |
| Protein-tyrosine-phosphatase | |
| Regulator of nonsense transcripts 1 | |
| Septin-9 | |
| S-formylglutathione hydrolase | |
| Signal recognition particle 14 kDa protein | |
| Succinate dehydrogenase [ubiquinone] flavoprotein subunit, mitochondrial | |
| Translocon-associated protein subunit delta | |
| Tubulin beta chain | |
| Tyrosine--tRNA ligase, cytoplasmic | |
| U1 small nuclear ribonucleoprotein A | |
| Ubiquitin carboxyl-terminal hydrolase 7 | |
| UMP-CMP kinase | |
| Vinculin | |
| Nicotinamide phosphoribosyltransferase | |
| Annexin A3 | |
| Eosinophil peroxidase | |
| Nuclear ubiquitous casein and cyclin-dependent kinase substrate 1 | |
| 14-3-3 protein gamma | |
| 26S protease regulatory subunit 4 | |
| AGR2 | |
| Cathepsin B | |
| EMILIN-1 | |
| Glutathione S-transferase omega-1 | |
| Heat shock protein HSP 90-alpha | |
| Heat shock protein HSP 90-beta | |
| Hydroxysteroid dehydrogenase-like protein 2 | |
| Mycophenolic acid acyl-glucuronide esterase, mitochondrial | |
| Proteasome activator complex subunit 1 | |
| Ras-related protein Rab-1A | |
| Ras-related protein Ral-B | |
| RNA-binding protein 14 | |
| Septin 11, isoform CRA_b | |
| Tubulin-specific chaperone A | |
| Metallothionein-2 | |
| B-cell receptor-associated protein 31 | |
| Ras-related protein Rab-5C | |
| Stress-induced-phosphoprotein 1 | |

Figure 3:
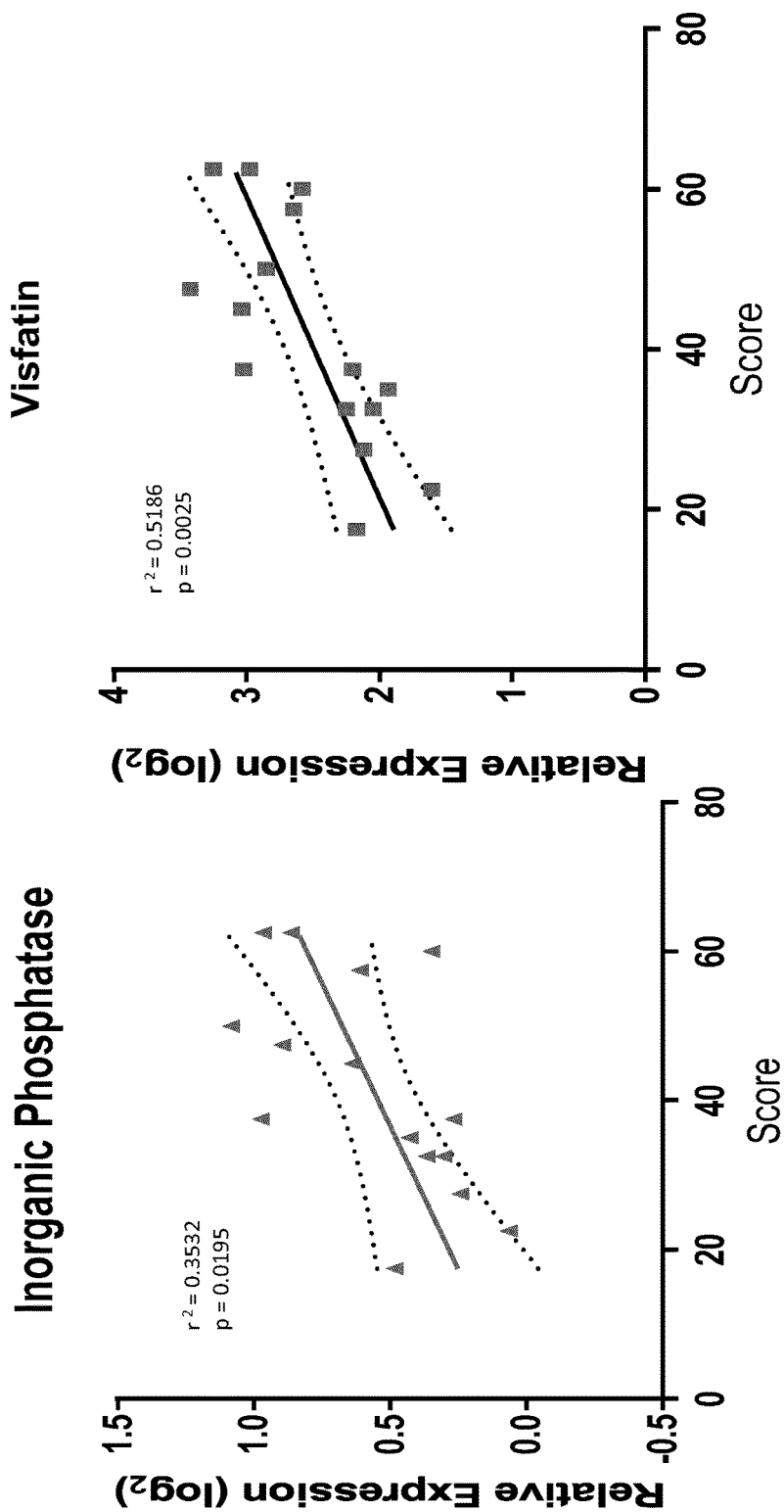
FIG. 3A is a graph of the relative expression of Inorganic Phosphatase as a function of CD severity score.
FIG. 3B is a graph of the relative expression of visfatin as a function of CD severity score.
FIG. 3C is a graph of the relative expression of MT-2 as a function of CD severity score.
FIG. 3D is a graph of the relative expression of HNRP H3 as a function of UC severity score.
Figure 3:
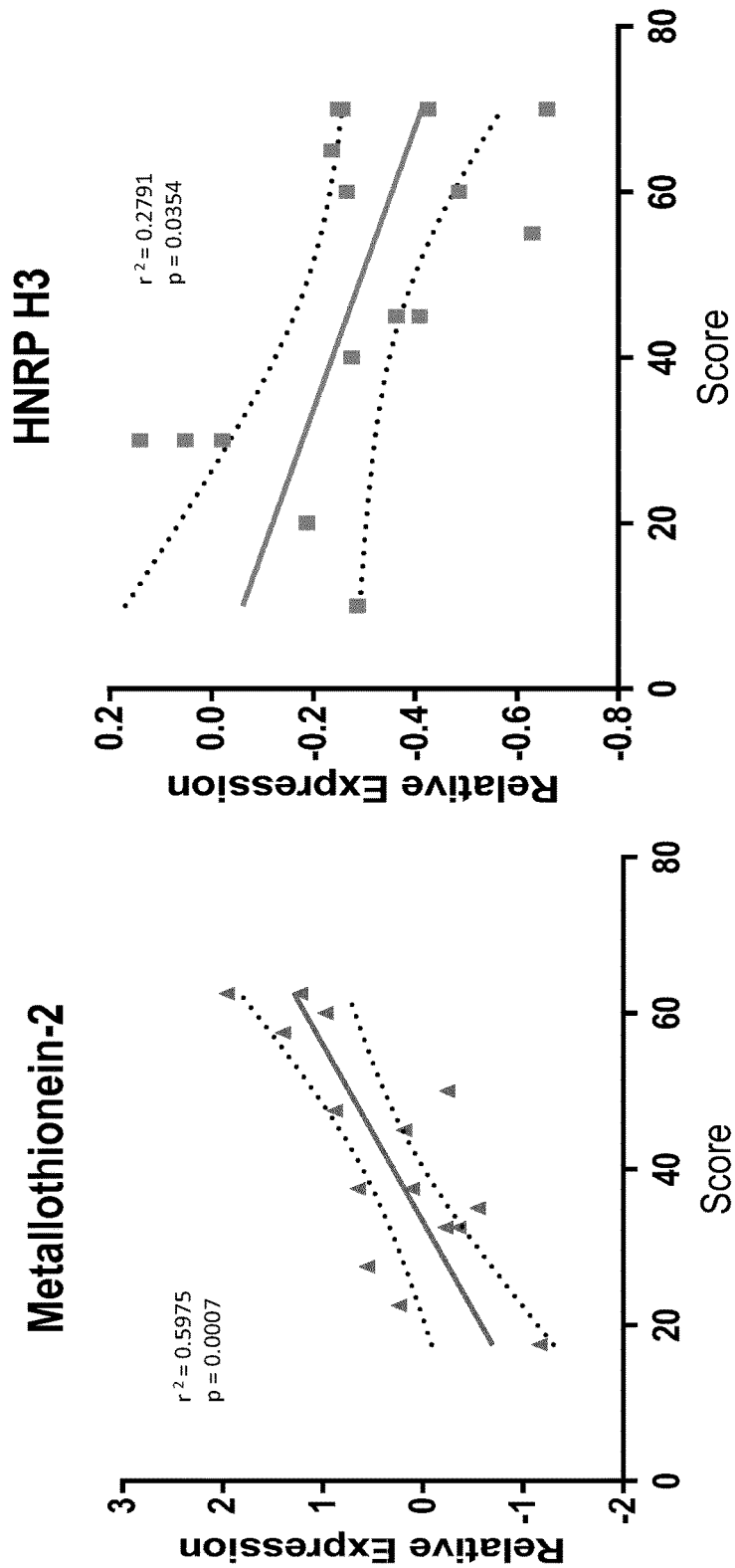

CD patient PCDAI severity scores showed significant correlation with 83 proteins, 10% of which are components of the protein ubiquitination pathway. In contrast, 10% of the 43 proteins that correlate with UC patient PUCAI scores are components of the mTOR signaling pathway. 15 of the CD-associated and 9 of the UC-associated proteins are regulated by HNF4A which was identified in a pediatric population to be associated with CD (Genes Immun 2012; 13:556-65) and is a UC susceptibility loci (Nat Genet 2009; 41:1330-4). There were eight proteins that correlate with severity score in both CD and UC patients, including RNA binding and integrin signaling proteins. Of the 118 proteins showing correlation with severity, 39 proteins were identified as biomarker candidates, four of which were in the panels for diagnosis or differentiation. Amongst the proteins biomarkers for control vs IBD the relative expression of both inorganic phosphatase and visfatin show significant correlation with CD severity (FIG. 3 A, B). Similarly, amongst the proteins biomarkers for UC v. CD, the relative expression protein metallothionein-2 (MT2) correlates with CD severity (FIG. 3C), whereas HNRP H3 is inversely related to UC severity (FIG. 3D). A previous study found a correlation between MT2 and grade of inflammation in adult IBD biopsies (J Pathol 2014; 233:89-100); the correlation with disease severity of the other 3 proteins is a new finding.

ELISA of visfatin and MT2 are consistent with proteomic data.

Figure 4:
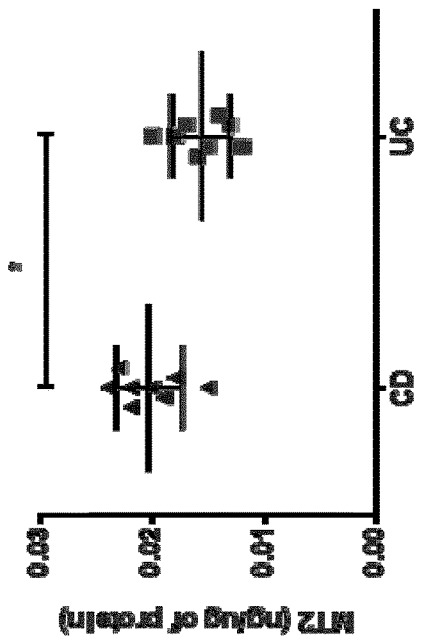
FIG. 4A is a chart of the amount of visfatin in control and IBD subjects measured by ELISA.
FIG. 4B is a chart of the amount of MT2 in CD and UC subjects measured by ELISA.
FIG. 4C is a graph of the amount of MT2 as a function of PCDAI score.
Figure 4:
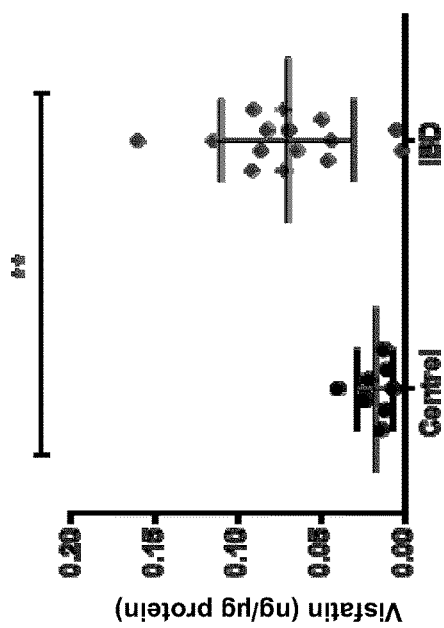
Figure 4:
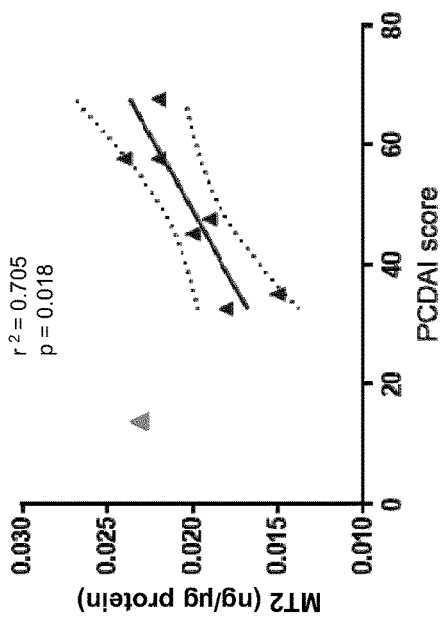

With the ultimate intent of translating our findings into the clinical setting, the absolute amount of two candidate biomarkers (one from each of the panels) were measured from patient biopsy samples. Using commercially available kits, the amount of visfatin and MT2 in a subset of validation cohort patient biopsies were measured by ELISA. The amount of visfatin was within the detection limits for 23/24 samples tested. The relative amounts of vistafin determined by proteomics in the discovery cohort is consistent in the validation cohort the ELISA (FIG. 4A), with a significantly higher amount in IBD patients. Similarly, MT2 was quantified in all samples tested from the validation cohort, and was significantly higher in CD than in UC patients in the validation proteomic and ELISA analyses (FIG. 4B). Consistent with the discovery cohort proteomic data, the ELISA results of the validation cohort showed correlation between the absolute amount of MT2 and the PCDAI in moderate or severe (PCDAI>30) CD patients (FIG. 4C). Due to the limited number of patients with mild CD, it cannot be determined whether the single mild CD patient with elevated MT2 levels is an outlier.

Example 2

The following figures that will now be described show the relative abundance of proteins in IBD, UC, CD as well as for different degree of severity of the disease that were identified by a variety of statistical models.

In an exemplary analysis 1949 proteins were accurately quantified from the patient biopsies; about 50% of these were found to be significantly different between patient groups by ANOVA. 296 proteins were determined by t-test to be significantly different between CD and UC patients; principle component analysis of resulted in segregation of control, CD and UC patient groups.

Figure 6:
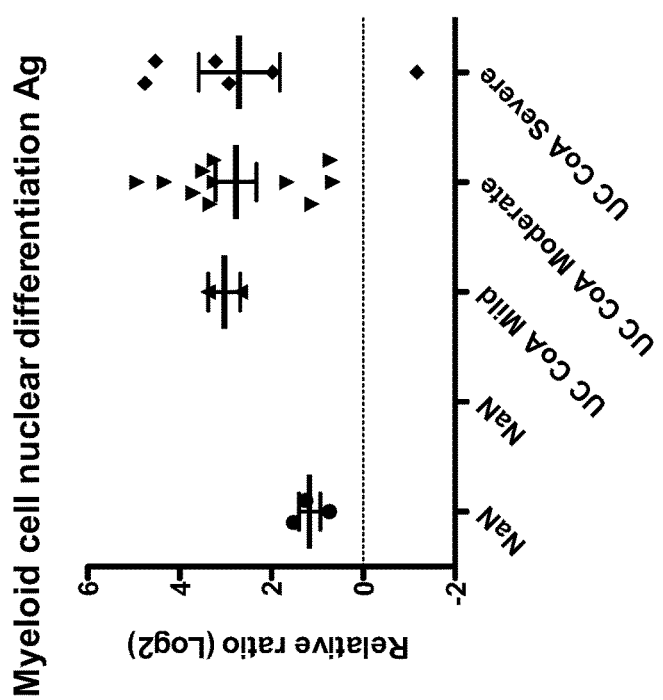
FIG. 6 is a chart of the relative ratio of Myeloid cell nuclear differentiation Ag for control and UC subjects with different levels of severity.
Figure 7:
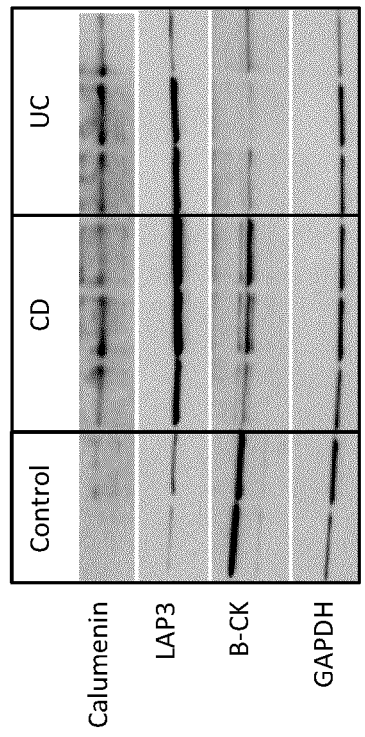
FIG. 7A is an immunoblot of validated biomarkers for pediatric IBD disease.
FIG. 7B is bar graph of relative densitometry of Calumenin in control, CD, UC subjects.
FIG. 7C is a chart of levels of Calumenin in control, CD, UC subjects.
FIG. 7D is bar graph of relative densitometry of LAP3 in control, CD, UC subjects.
FIG. 7E is a chart of levels of LAP3 in control, CD, UC subjects.
FIG. 7F is bar graph of relative densitometry of B-CK in control, CD, UC subjects.
FIG. 7G is a chart of levels of B-CK in control, CD, UC subjects.
Figure 7C:
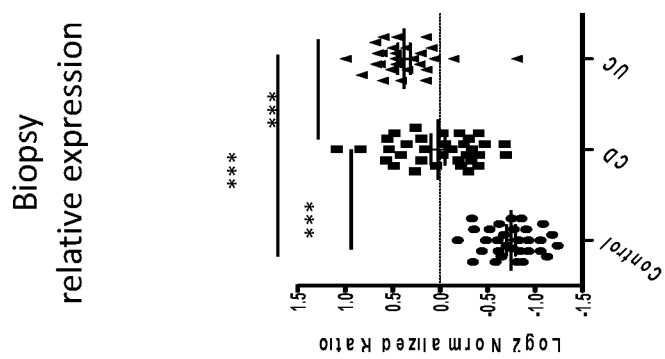
Figure 7B:
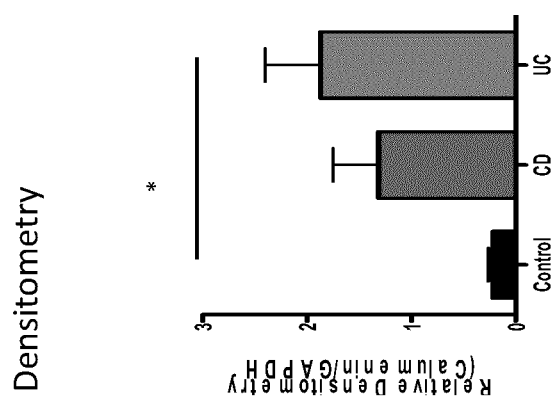
Figure 7E:
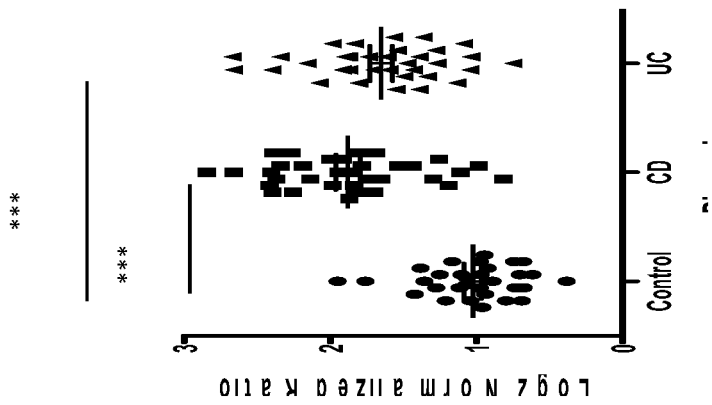
Figure 7D:
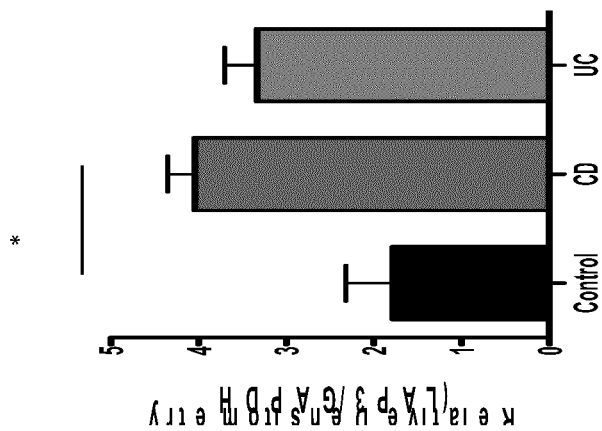
Figure 7G:
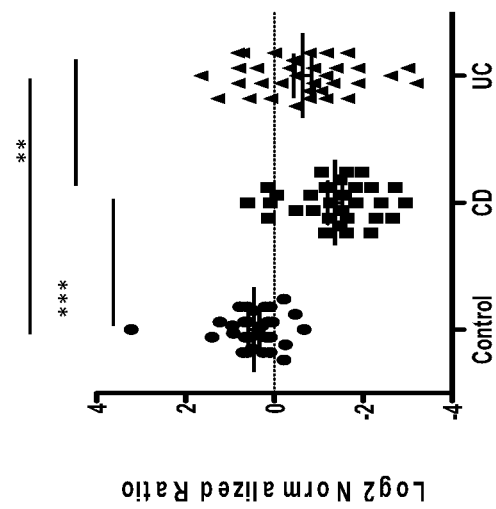
Figure 7F:
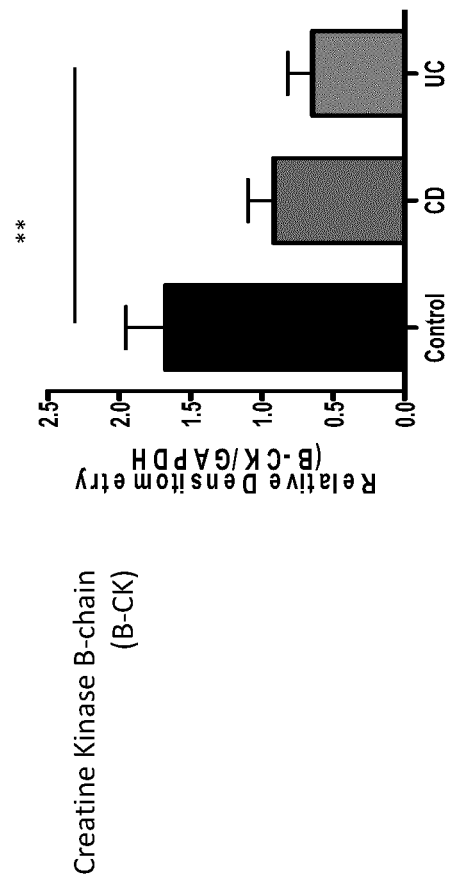

FIGS. 5 and 6 show a number of proteins that are more abundant in CD and UC affected individuals than normal controls. FIG. 7 shows an additional analysis where calumenin, LAP3 and B-CK are identified as biomarkers for pediatric IBD.

FIG. 8 shows a number of proteins that exhibit a differential abundance in CD and UC patients.

FIG. 9 shows a number of proteins that exhibit a differential abundance in patients with different levels of UC disease severity.

Figure 10E:
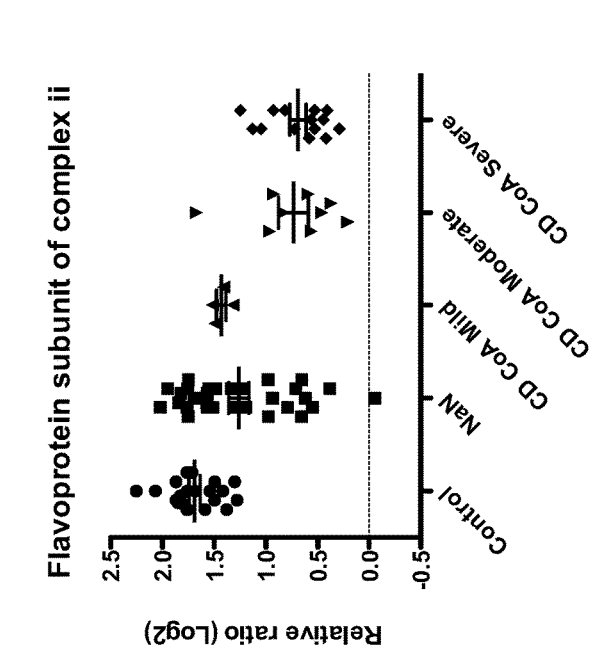
FIG. 10 A-G are charts of relative ratios of proteins identified as biomarkers for the severity of CD.
Figure 10F:
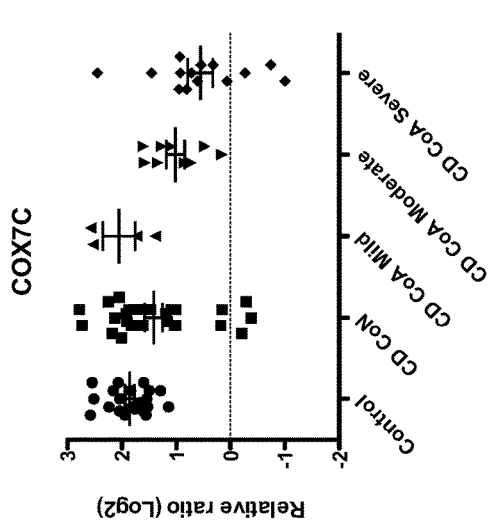
Figure 10G:
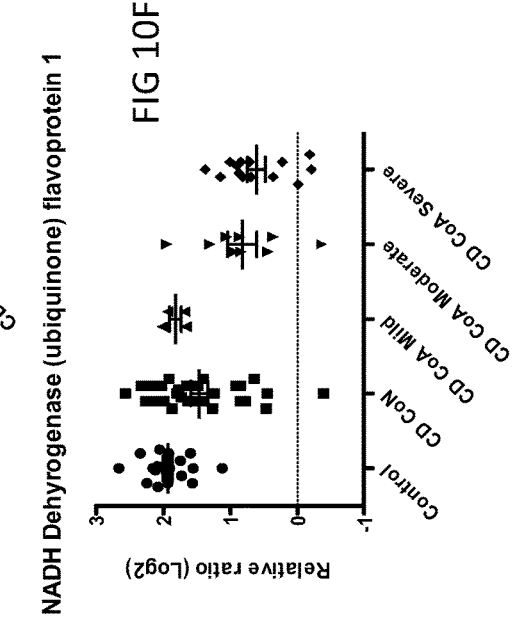
Figure 11E:
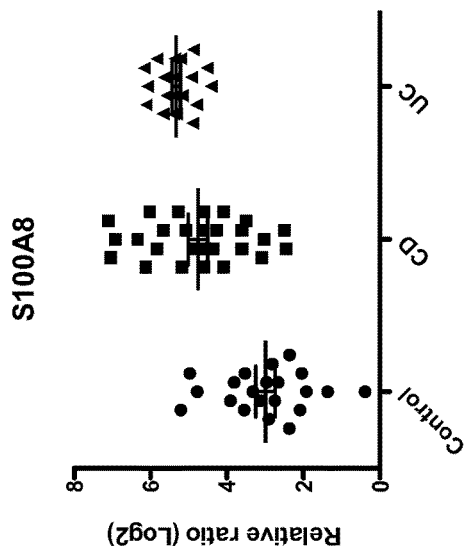
FIG. 11 A-R are charts of relative ratios of proteins identified as biomarkers for distinguishing UC and CD using PCA analysis.
Figure 11F:
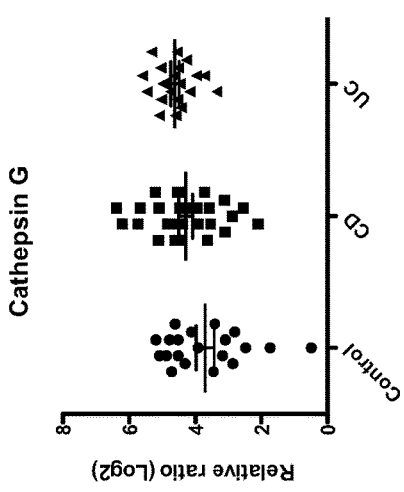
Figure 11G:
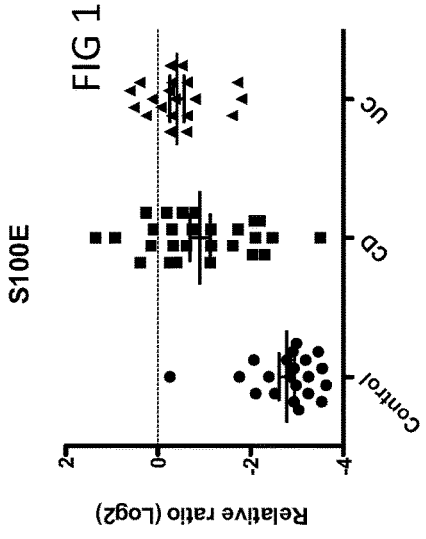
Figure 11H:
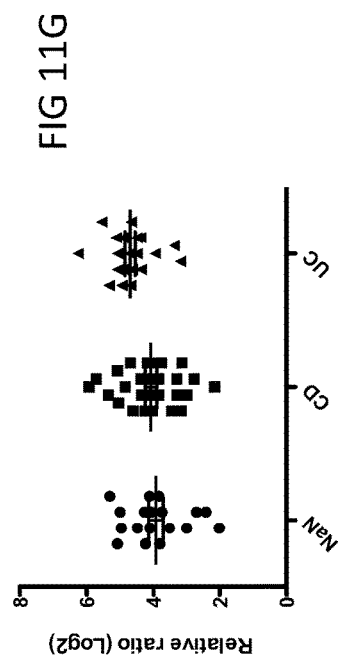
Figure 11R:
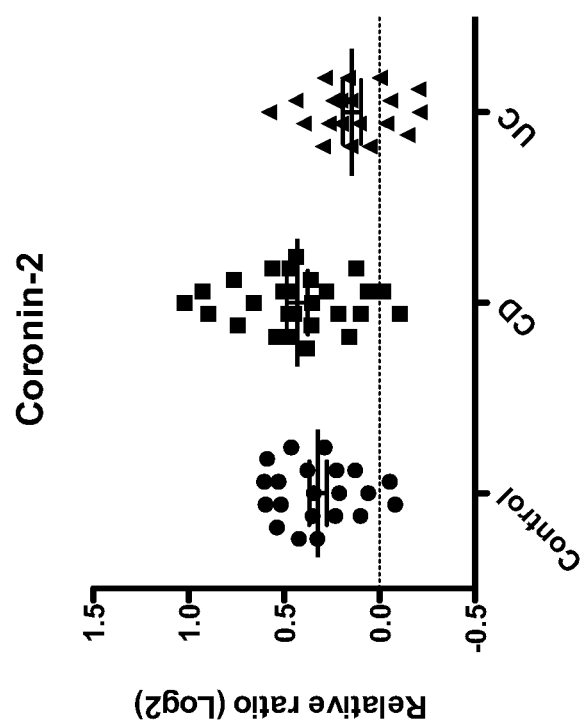

FIG. 10 shows a number of proteins that exhibit a differential abundance in patients with different levels of CD disease severity.

In yet another analysis FIG. 11 shows proteins identified by Principal Component Analysis (PCA) that exhibit differential abundance in control vs CD vs UC and provide examples of potential protein markers from this analysis.

Figure 12I:
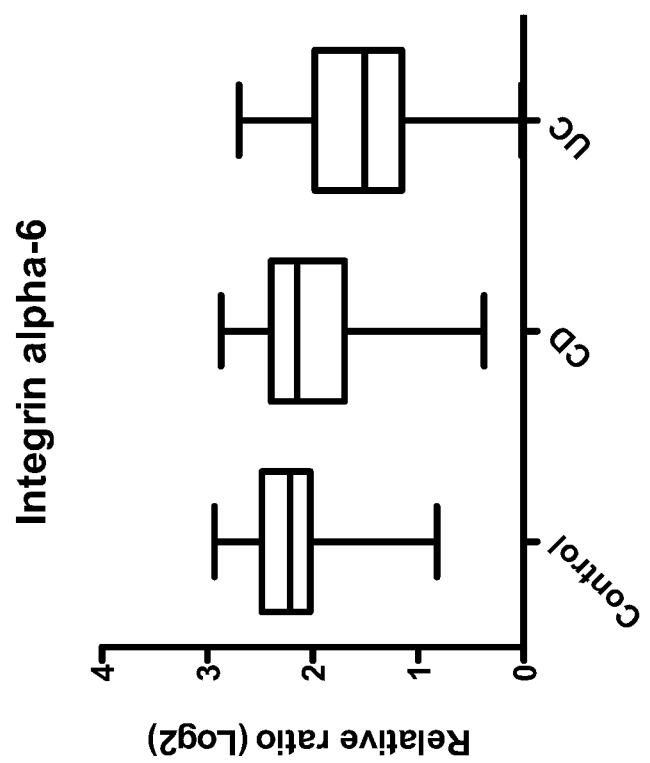
FIG. 12 A-I are charts of relative ratios of proteins identified as biomarkers for distinguishing UC and CD using PCA analysis.
Figure 13I:
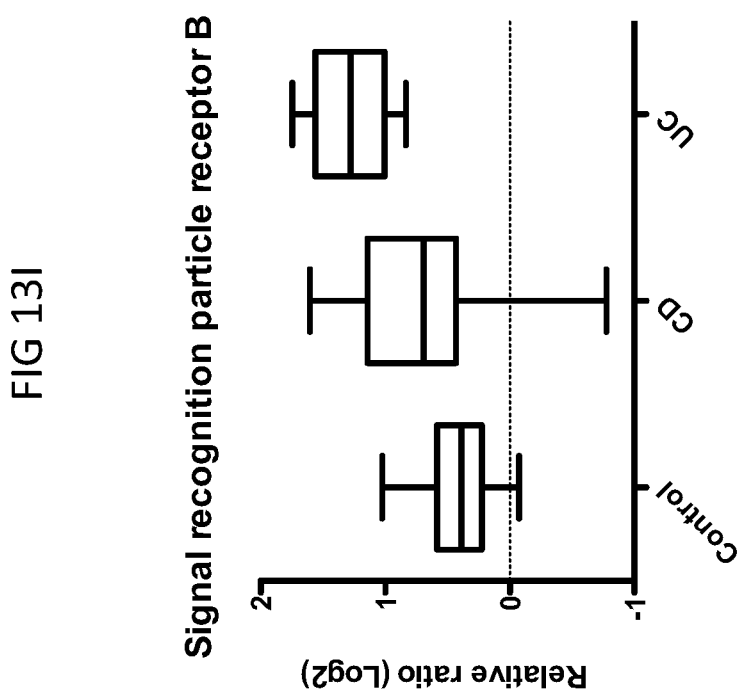
FIG. 13 A-I are charts of relative ratios of proteins identified as biomarkers for distinguishing UC and CD using Roccet analysis.
Figure 15A:
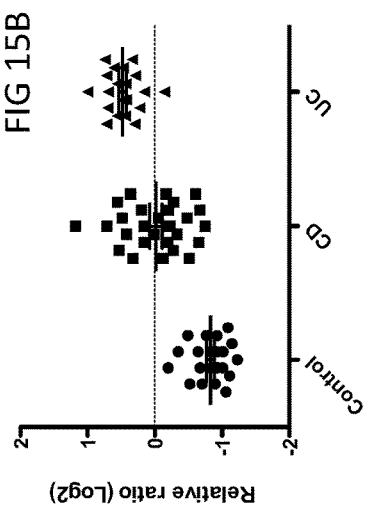
FIG. 15 A-K are charts of relative ratios of proteins identified as biomarkers for distinguishing UC and CD using PLSDA analysis showing high level UC compare to CD.
Figure 15B:
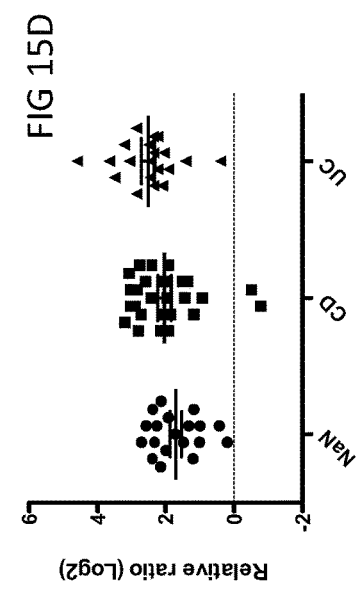
Figure 15C:
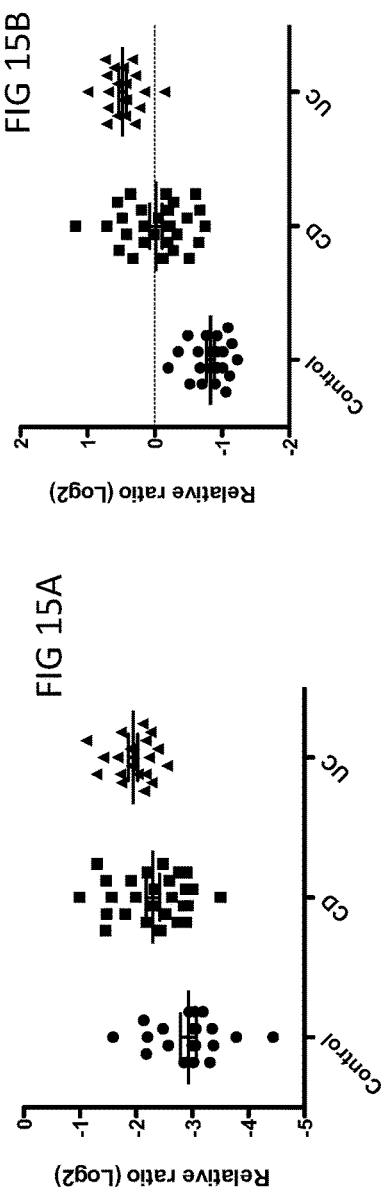
Figure 15D:
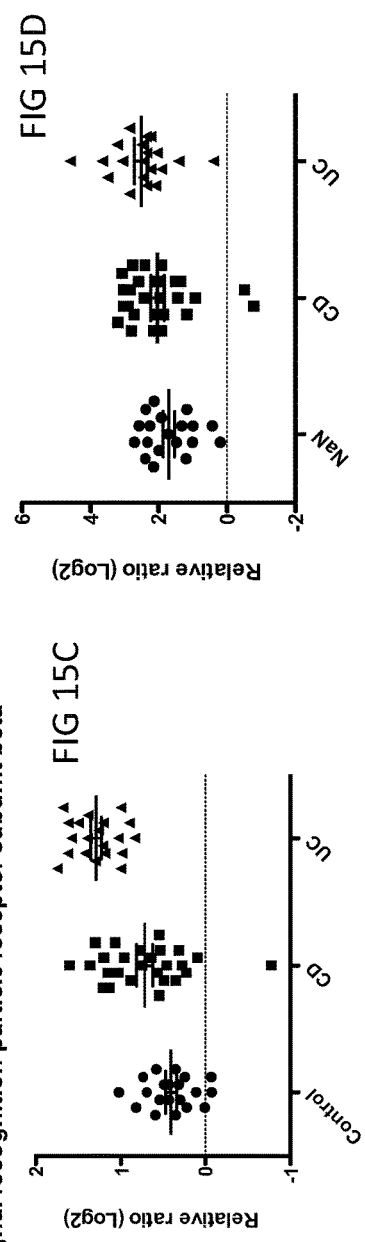
Figure 17J:
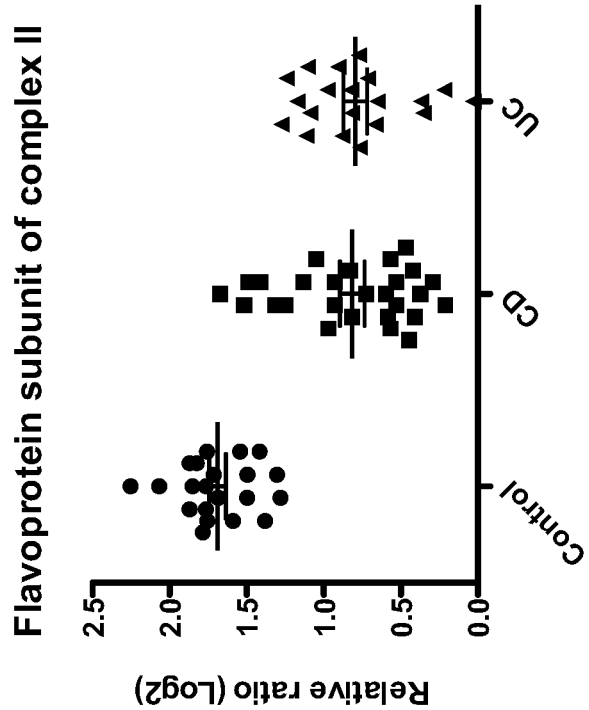
FIG. 17 A-J are charts of relative ratios of proteins identified as biomarkers for distinguishing control, UC and CD using PLSDA analysis.
Figure 17I:
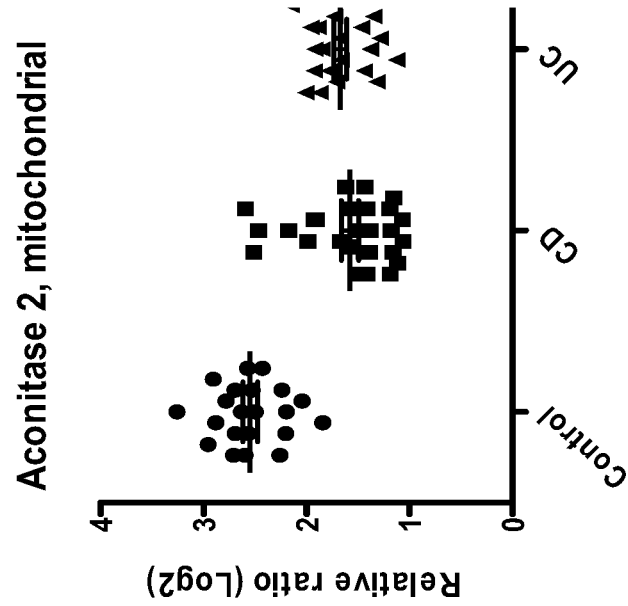

Another example of proteins identified by PCA of which 418 proteins that are significantly different by Ttest between CD and UC patients were used. The list of 77 proteins that are most responsible for PCA grouping were identified and considered potential biomarkers. FIG. 12 provides examples of potential protein markers from this analysis.

In yet another analysis, the segregation of CD vs UC was analyzed using Roccet. ROC curves were generated by Monte-Carlo cross validation (MCCV) using balanced sub-sampling. In each MCCV, two thirds (⅔) of the (max) important features are then used to build classification models which is validated on ⅓ of the samples that were left out. The procedures were repeated multiple times to calculate the performance and confidence interval of each model. A similar analysis was performed using ROC/Partial Least Squares Discriminant Analysis (PLSDA). Similar analyses were performed to show the segregation of controls vs disease (IBD), control vs CD and control vs UC. FIGS. 13, 14, 15, 16 and 17 show examples of protein markers identified using this analysis.

Figure 18B:
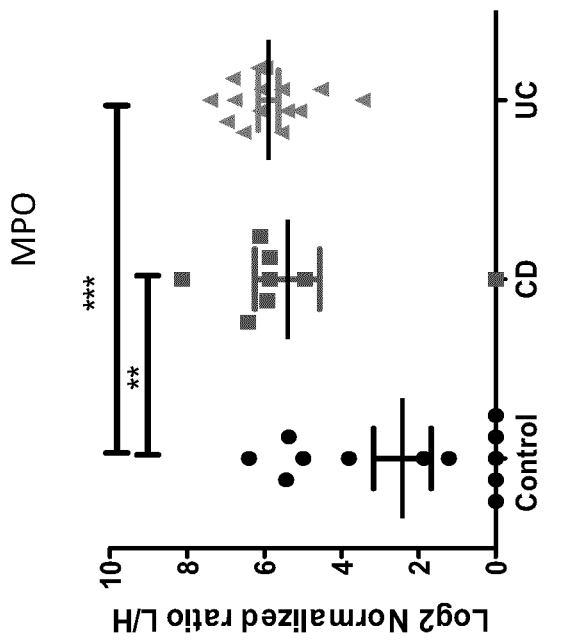
FIG. 18 A-K are charts of normalized ratios of proteins identified as biomarkers for distinguishing control, IBD, UC and CD.
Figure 18A:
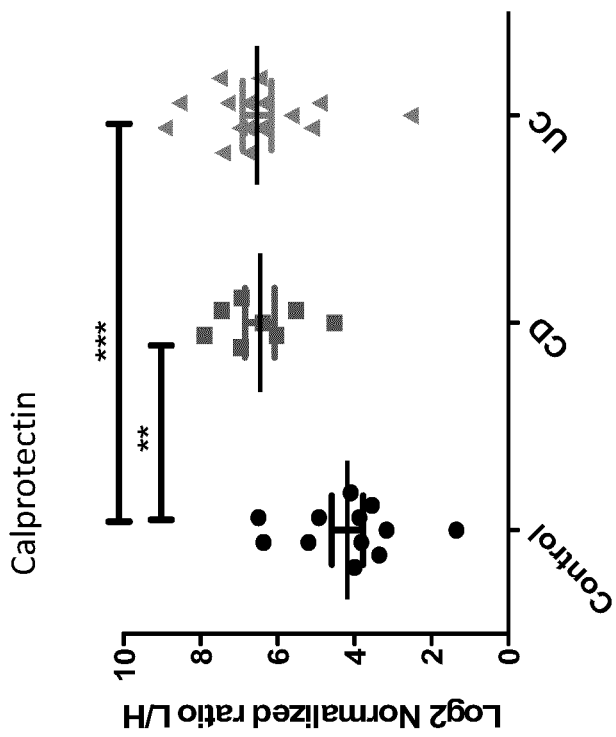
Figure 18F:
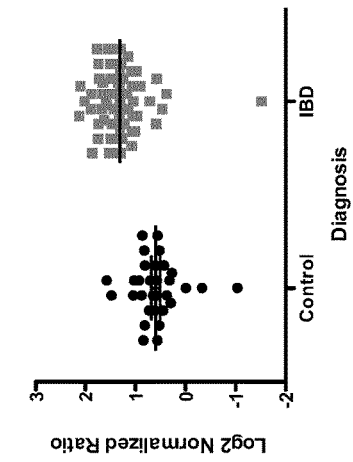
Figure 18G:
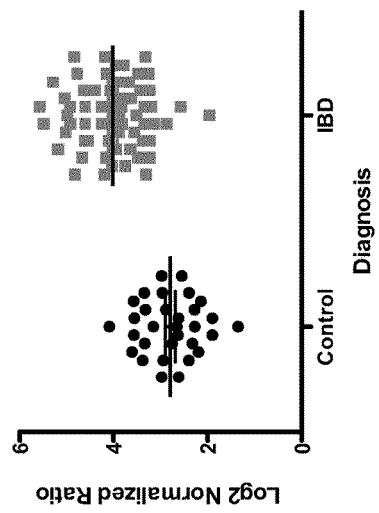
Figure 18:
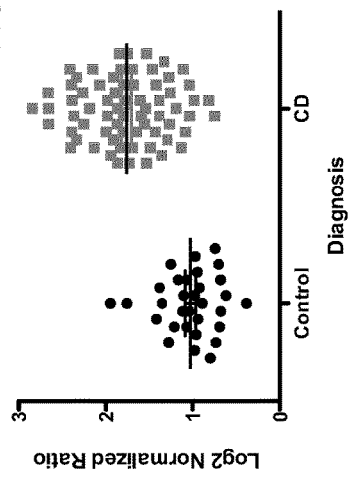
Figure 18:
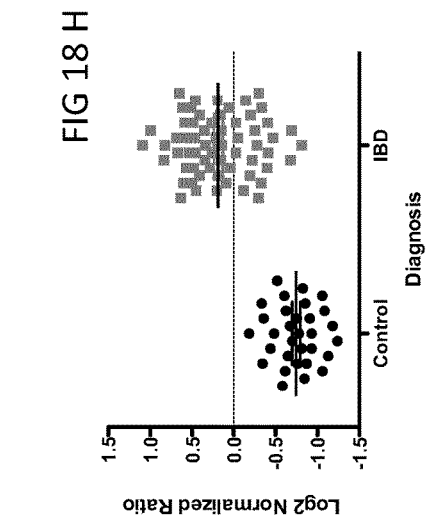
Figures 18J, 18K:
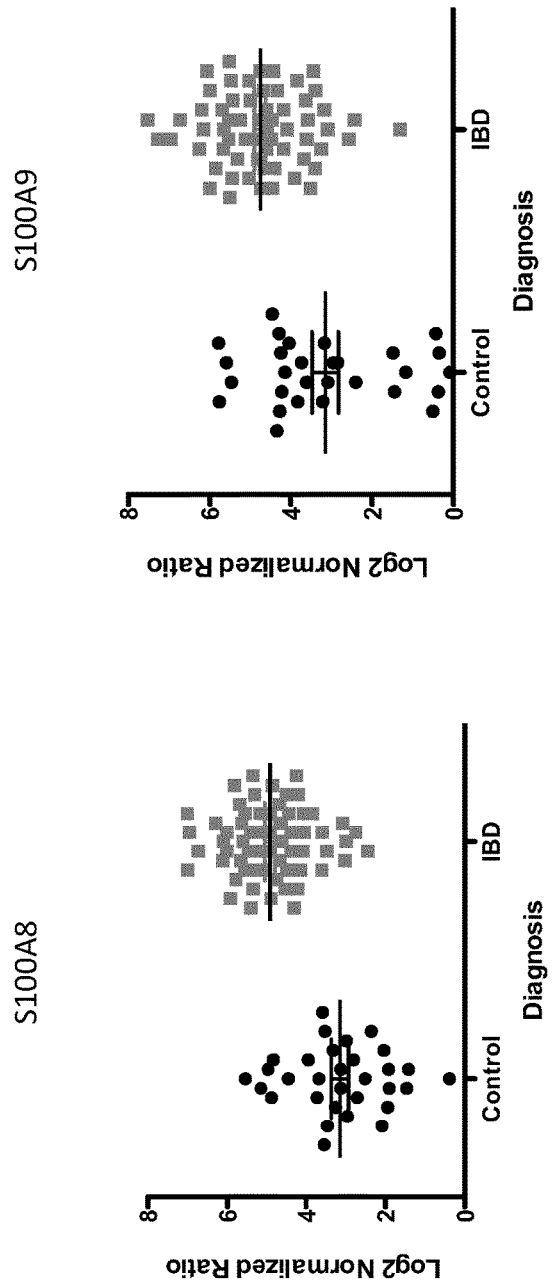

A further exemplary analysis was performed using ROC that shows the elevated levels of certain proteins in IBD (FIG. 18).

The diagnostic markers described above can be used in a method for classifying a sample as being associated with IBD, UC or CD. The method comprises the steps of determining a presence or level of one or more of the diagnostic markers and comparing the presence or level to samples from IBD, UC or CD patients and/or normal patients. A combination of diagnostic markers may be used and may also further be combined with a standard diagnostic results derived from a disease activity index.

There is also provided a method for treating IBD or UC or CD disease wherein a diagnosis is first established using one or more of the disease markers described above and determining a course of treatment. The treatment may consist in administering to the patient a pharmaceutically effective amount of a compound selected from aminosalycylates, immunomodulators, anti-integrins, anti-cytokines, enteral feed programs, steroids, corticosteroids, antibiotics, anti-TNFα, bismuth or a combination thereof.

The following is an exemplary protocol for mass-spec analysis used to identify markers. It will be appreciated that the person skilled in the art may implement modifications of this protocol in order to adapt it to particular situations or sample characteristics without deviating from the invention.

Stable Isotope Labeling by Amino Acids in Cell Culture (SILAC):

Human hepatic HuH7 cells (HuH-7), human embryonic kidney 293 cells (HEK-293) and human colorectal cancer 116 cells (HCT-116) were individually grown at 37° C. in a 5% CO2 humidified incubator. SILAC medium was prepared as follows: DMEM lacking lysine, arginine and methionine was custom prepared by AthenaES (Baltimore, Md., USA) and supplemented with 30 mg/L methionine (Sigma Aldrich; Oakville, ON, CAN), 10% (v/v) dialyzed FBS (GIBCO-Invitrogen; Burlington, ON,CAN), 1 mM sodium pyruvate (Gibco-lnvitrogen), 28 µg/mL gentamicin (Gibco-Invitrogen), and $[^{13}C_6, ^{15}N_2]$-L-lysine, $[^{13}C_6, ^{15}N_4]$-L-arginine (heavy form of amino acids; Heavy Media) from Sigma Aldrich (Oakville, ON, CAN) at final concentrations of 42 mg/L and 146 mg/L for arginine and lysine respectively. For HCT-116, the concentration of arginine was increased to 84 mg/L. Cells were grown for at least 10 doublings in SILAC media to allow for complete incorporation of the isotopically labeled amino acids into the cells.

Determination of the rate of SILAC amino acids incorporation into HuH-7, HEK-293 and HCT-116 cells:

Cells were grown to 80% confluency in SILAC medium ($5 \times 10^6$ cells were plated in 10-cm dish). Next, the cells were washed twice with ice-cold phosphate-buffered saline and lyzed by addition of 1 mL of 1×RIPA buffer (50 mM Tris (pH 7.6), 150 mM NaCl, 1% (v/v) NP-40, 0.5% (w/v) deoxycholate, 0.1% (w/v) SDS with protease inhibitor cocktail (Complete Mini Roche; Mississauga, ON,CAN) and phosphatase inhibitor (PhosStop Roche tablet). The lysates were then transferred to 15 mL conical tubes and the proteins were precipitated by addition of 5 mL ice-cold acetone followed by incubation at −20° C. overnight. Proteins were collected by centrifugation (3000×g, 10 min, 4° C.), washed with ice-cold acetone two times, and the protein pellets were resolubilized in 300 µL of a 50 mM $NH_4HCO_3$ solution containing 8 M urea. Protein concentrations were determined by the Bradford dye-binding method using Bio- Rad's Protein Assay Kit (Mississauga, ON, CAN). For the general in-solution digestion, 200 μg of protein lysates were reconstituted in 50 mM NH₄HCO₃ (200 μL) and proteins were reduced by mixing with 5 μL of 400 mM DTT at 56° C. for 15 min. The proteins were then subjected to alkylation by mixing with 20 μL of 400 mM iodoacetamide in darkness (15 min at room temperature) followed by addition of 800 μL of 50 mM NH₄HCO₃ to reduce the urea concentration to ~0.8 M. Next, the proteins were digested with TPCK-trypsin solution (final ratio of 1:20 (w/w, trypsin:protein) at 37° C. for 18 h. Finally, the digested peptides were desalted using $C_{18}$ Sep-Pack cartridges (Waters), dried down in a speed-vac, and reconstituted in 0.5% formic acid prior to mass spectrometric analysis (as described below) and the determination of labeling efficiency. The incorporation efficiency was calculated according to the following equation: (1−1/Ratio(H/L)); where H and L represents the intensity of heavy and light peptides detected by mass-spectrometry, respectively. Labeling was considered complete when values reached at least 95% for each cell type.

Proteomic Analysis of Biopsies Using Super-SILAC-Based Quantitative Mass Spectrometry:

Biopsies were lysed in 4% SDS (sodium dodecyl sulfate), 50 mM Tris-HCl (pH 8.0) supplemented with proteinase inhibitor cocktail (Roche) and homogenized with a Pellet pestle. The lysates were sonicated 3 times with 10 s pulses each with at least 30 s on ice between each pulse. Protein concentrations were determined using the Bio-Rad DC Protein Assay. The proteins were processed using the Filter Aided Sample Preparation Method (FASP) as previously described with some modifications. Colon tissue lysates (45 μg of proteins) and heavy SILAC-labeled cell lysates (15 μg from each HuH-7, HEK-293 and HCT-116 cells) were mixed at a 1:1 weight ratio and transferred into the filter. The samples were centrifuged (16,000×g, 10 min), followed by two washes of 200 μL 8 M urea, 50 mM Tris-HCl pH 8.0. Samples were then reduced by incubation in 200 μL of 8 M urea, 50 mM Tris-HCl (pH 8.0) supplemented with 20 mM dithiothreitol. After centrifugation, samples were subjected to alkylation by adding 200 μL of 8 M urea, 50 mM Tris-HCl pH 8.0, containing 20 mM iodoacetamide (30 min at room temperature protected from light). Samples were washed using 200 μL 8 M urea, 50 mM Tris-HCl pH 8.0 (twice) to remove excess SDS. To further dilute urea, two washes of 200 μL 50 mM Tris-HCl pH 8.0 were performed. For the trypsin digest, samples were incubated in 200 μL of 50 mM Tris-HCl pH 8.0, containing 5 μg of Trypsin (TPCK Treated, Worthington) on a shaker (250 rpm) at 37° C. overnight. Finally, 200 μL of 50 mM Tris-HCl pH 8.0 was added to elute the peptides by centrifugation (twice). Peptides were fractionated, using an in-house constructed SCX column with five pH fractions (pH 4.0, 6.0, 8.0, 10.0, 12.0). The buffer composition was 20 mM boric acid, 20 mM phosphoric acid, and 20 mM acetic acid, with the pH adjusted by using 1 M NaOH). Finally, the fractionated samples were desalted using in-house $C_{18}$ desalting cartridges and dried in a speed-vac prior to LC-MS analysis.

Mass-Spectrometry Analyses:

All resulting peptide mixtures were analyzed by high-performance liquid chromatography/electrospray ionization tandem mass spectrometry (HPLC-ESI-MS/MS). The HPLC-ESI-MS/MS consisted of an automated Ekspert™ nanoLC 400 system (Eksigent, Dublin, Calif., USA) coupled with an LTQ Velos Pro Orbitrap Elite mass spectrometer (ThermoFisher Scientific, San Jose, Calif.) equipped with a nano-electrospray interface operated in positive ion mode. Briefly, each peptide mixture was reconstituted in 20 μL of 0.5% (v/v) formic acid and 12 μL was loaded on a 200 μm×50 mm fritted fused silica pre-column packed in-house with reverse phase Magic $C_{18}$AQ resins (5 μm; 200 Å pore size; Dr. Maisch GmbH, Ammerbuch, Germany). The separation of peptides was performed on an analytical column (75 μm×10 cm) packed with reverse phase beads (3 μm; 120 Å pore size; Dr. Maisch GmbH, Ammerbuch, Germany) using a 120 min gradient of 5-30% acetonitrile (v/v) containing 0.1% formic acid (v/v) (JT Baker, Phillipsburg N.J., USA) at an eluent flow rate of 300 nL/min. The spray voltage was set to 2.2 kV and the temperature of heated capillary was 300° C. The instrument method consisted of one full MS scan from 400 to 2000 m/z followed by data-dependent MS/MS scan of the 20 most intense ions, a dynamic exclusion repeat count of 2, and a repeat duration of 90 s. The full mass was scanned in an Orbitrap analyzer with R=60,000 (defined at m/z 400), and the subsequent MS/MS analyses were performed in LTQ analyzer. To improve the mass accuracy, all the measurements in the Orbitrap mass analyzer were performed with on-the-fly internal recalibration ("Lock Mass"). The charge state rejection function was enabled with charge states "unassigned" and "single" states rejected. All data were recorded with Xcalibur software (ThermoFisher Scientific, San Jose, Calif.).

Database Search and Bioinformatic Analysis:

Raw files can be processed and analyzed by MaxQuant, Version 1.5.1 against the decoy Uniport-human database (downloaded 2014 Jul. 11), including commonly observed contaminants. The protein-group file was imported into Persus (version 1.3.0.4) for data statistical analysis.

What is claimed is:

1. A method of detecting inflammatory bowel disease in a subject comprising:
   providing a sample obtained from the gut of a subject;
   detecting in said sample a level of each of the following markers: fatty acid-binding protein, visfatin, UDP-Glucose 6-dehydrogenase, leucine-rich PPR motif-containing protein, and inorganic pyrophosphatase.

2. A method for treating inflammatory bowel disease in a patient comprising:
   determining whether inflammatory bowel disease has been detected in said subject by performing the method of claim 1 and administering to said patient a compound pharmaceutically effective against inflammatory bowel disease.

3. The method of claim 2, wherein said administering comprises administering a pharmaceutically effective amount of a compound selected from the group consisting of aminosalycylates, immunomodulators, anti-integrins, anti-cytokines, enteral feed programs, steroids, corticosteroids, antibiotics, anti-TNFa, and bismuth, or a combination thereof.

4. The method of claim 1, further comprising obtaining further information regarding the presence of inflammatory bowel disease in said subject by combining said detecting of said markers with a disease activity index specific for inflammatory bowel disease.

5. The method of claim 1, wherein said obtaining a level is by using an immunoassay.

6. The method of claim 5, wherein said immunoassay is an ELISA.

7. A method for treating inflammatory bowel disease in a patient comprising:
   requesting an analysis of a sample according to the method of claim 1 and administering to the patient a compound selected from the group consisting of aminosalycylates, immunomodulators, anti-integrins, anti-cytokines, enteral feed programs, steroids, corticosteroids, antibiotics, anti-TNFα, and bismuth, or combinations thereof, if the sample is associated with inflammatory bowel disease.

* * * * *